US009700602B2

(12) United States Patent
Malakhov et al.

(10) Patent No.: US 9,700,602 B2
(45) Date of Patent: Jul. 11, 2017

(54) MICROPARTICLE FORMULATIONS FOR DELIVERY TO THE LOWER AND CENTRAL RESPIRATORY TRACT AND METHODS OF MANUFACTURE

(71) Applicant: Ansun Biopharma, Inc., San Diego, CA (US)

(72) Inventors: Michael P. Malakhov, San Francisco, CA (US); Tiejun Li, San Diego, CA (US)

(73) Assignee: Ansun Biopharma, Inc., San Diego, CA (US)

( * ) Notice: Subject to any disclaimer, the term of this patent is extended or adjusted under 35 U.S.C. 154(b) by 0 days.

(21) Appl. No.: 15/156,268

(22) Filed: May 16, 2016

(65) Prior Publication Data

US 2016/0324941 A1 Nov. 10, 2016

Related U.S. Application Data

(63) Continuation of application No. 13/931,419, filed on Jun. 28, 2013, now abandoned.

(60) Provisional application No. 61/779,653, filed on Mar. 13, 2013, provisional application No. 61/665,807, filed on Jun. 28, 2012.

(51) Int. Cl.

| | |
|---|---|
| ***A61K 38/47*** | (2006.01) |
| ***A61K 9/16*** | (2006.01) |
| ***A61K 9/00*** | (2006.01) |
| ***A61K 38/18*** | (2006.01) |
| *C07K 14/36* | (2006.01) |

(52) U.S. Cl.

CPC ............ *A61K 38/47* (2013.01); *A61K 9/0075* (2013.01); *A61K 9/1611* (2013.01); *A61K 9/1617* (2013.01); *A61K 9/1623* (2013.01); *A61K 9/1682* (2013.01); *A61K 38/18* (2013.01); *C12Y 302/01018* (2013.01); *C07K 14/36* (2013.01); *C07K 2319/00* (2013.01)

(58) Field of Classification Search

CPC .... C07K 14/36; C07K 2319/00; A61K 38/47; A61K 9/1617; A61K 9/1623; A61K 9/1682; A61K 38/18; A61K 9/1611; A61K 9/0075; C12Y 302/01018

See application file for complete search history.

(56) References Cited

U.S. PATENT DOCUMENTS

| | | | | |
|---|---|---|---|---|
| 3,439,089 | A | 4/1969 | Cherkas et al. | |
| 5,033,252 | A | 7/1991 | Carter | |
| 5,052,558 | A | 10/1991 | Carter | |
| 5,145,702 | A | 9/1992 | Stark et al. | |
| 5,323,907 | A | 6/1994 | Kalvelage | |
| 5,981,719 | A | 11/1999 | Woiszwillo et al. | |
| 6,051,256 | A | 4/2000 | Platz et al. | |
| 6,063,910 | A | 5/2000 | Debenedetti et al. | |
| 6,090,925 | A | 7/2000 | Woiszwillo et al. | |
| 8,623,419 | B2 | 1/2014 | Malakhov et al. | |
| 2002/0037316 | A1 | 3/2002 | Weers et al. | |
| 2002/0142985 | A1 | 10/2002 | Dwek et al. | |
| 2005/0004020 | A1 | 1/2005 | Yu et al. | |
| 2005/0112751 | A1 | 5/2005 | Fang et al. | |
| 2005/0234114 | A1 | 10/2005 | Lee | |
| 2005/0244503 | A1 | 11/2005 | Rabinow et al. | |
| 2006/0260777 | A1 | 11/2006 | Rashba-Step et al. | |
| 2007/0190163 | A1 | 8/2007 | Malaknov et al. | |
| 2007/0207210 | A1 | 9/2007 | Brown et al. | |
| 2007/0231398 | A1 | 10/2007 | Van et al. | |
| 2008/0075708 | A1 | 3/2008 | Yu et al. | |
| 2009/0098207 | A1 | 4/2009 | Malakhov et al. | |
| 2010/0166874 | A1* | 7/2010 | Malakhov ............ | A61K 9/0073 424/499 |
| 2011/0003001 | A1 | 1/2011 | Baker | |
| 2011/0171132 | A1* | 7/2011 | Fang .................... | A61K 9/0014 424/9.2 |
| 2011/0172141 | A1 | 7/2011 | Naylor et al. | |
| 2012/0116062 | A1 | 5/2012 | Malakhov et al. | |
| 2015/0290134 | A1 | 10/2015 | Malakhov et al. | |
| 2015/0359746 | A1 | 12/2015 | Malakhov et al. | |

FOREIGN PATENT DOCUMENTS

| | | |
|---|---|---|
| CN | 1729013 | 2/2006 |
| EP | 0542314 | 5/1993 |
| JP | 2003-505342 | 2/2003 |
| JP | 2003513710 | 4/2003 |
| JP | 2008-512117 | 4/2008 |
| WO | WO 91/05792 | 5/1991 |
| WO | WO 9420856 | 9/1994 |
| WO | WO 9629998 | 10/1996 |
| WO | WO 9806279 | 2/1998 |
| WO | WO 0029096 | 5/2000 |
| WO | 0128524 | 4/2001 |
| WO | WO 01/34113 | 5/2001 |

(Continued)

OTHER PUBLICATIONS

US 5,849,884, 11/1999, Woiszwillo et al. (withdrawn)

Agrawal et al., "Basis of rise in intracellular sodium in airway hyperresponsiveness and asthma," Lung, 183:375-387, (2005).

Alcock, R., et al., "Modifying the release of leuprolide from spray dried OED microparticles," Journal of Control Release, 82(2-3):429-440, (2002).

Barbey-Morel, C.L., et al., "Role of respiratory tract proteases in infectivity of influenza A virus," Journal of Infectious Diseases, 155:667-672, (1987).

Bot A.I, et al., "Novel lipid-based hollow-porous microparticles as a platform for immunoglobulin delivery to the respiratory tract," Pharmaceutical Research, 17(3):275-283, (2000).

(Continued)

*Primary Examiner* — Suzanne Ziska

(74) *Attorney, Agent, or Firm* — Fish & Richardson P.C.

(57) ABSTRACT

Microparticle formulations of a sialidase fusion protein are produced by contacting an aqueous solution of a protein or other active agent with an organic solvent, a counterion and a scavenging agent, and chilling the solution. The microparticles are useful for preparing stable, uniform pharmaceuticals of predetermined defined dimensions.

23 Claims, No Drawings

(56) References Cited

FOREIGN PATENT DOCUMENTS

| | | |
|---|---|---|
| WO | WO 2004047735 | 6/2004 |
| WO | WO 2005035088 | 4/2005 |
| WO | WO 2005/046721 | 5/2005 |
| WO | WO 2005105278 | 11/2005 |
| WO | WO 2005105293 | 11/2005 |
| WO | WO 2005/112893 | 12/2005 |
| WO | WO 2006031291 | 3/2006 |
| WO | 2006045795 | 5/2006 |
| WO | WO 2007061849 | 5/2007 |
| WO | WO 2007114881 | 10/2007 |
| WO | WO 2009015286 | 1/2009 |
| WO | WO 2011/057081 | 5/2011 |

OTHER PUBLICATIONS

Cryan S.A., "Carrier-based strategies for targeting protein and peptide drugs to the lungs," American Association of Pharmaceutical Scientists PharmSci AAPS [electronic resource], 7(1):E20-E41, (2005).

Edwards D.A. et al., "Large porous particles for pulmonary drug delivery," Science, 276(5320):1868-1871, (1997).

Garcia-Contreras, L, et al., "Evaluation of novel particles as pulmonary delivery systems for insulin in rats," American Association of Pharmaceutical Scientists PharmSci AAPS [electronic resource], 5(2):E9, (2003).

*Genetic Engineering News* Featuring a Fill Corporate & Product Profile on NexBio & Fludase (PDF), (PDF is attached, called "gennexbio"), (accessed on Jun. 12, 2007) (2005).

Goger, B., et al., "Different affinities of glycosaminoglycan oligosaccharides for monomeric and dimeric interleukin-8: a model for chemokine regulation at inflammatory sites," Biochemistry, 41:1640-1646, (2002).

Grenha A, et al., "Microencapsulated chitosan nanoparticles for lung protein delivery," European Journal of Pharmaceutical Sciences, 25(4-5):427-437, (2005).

Huntington, J.A., et al., "Structure of a serpin-protease complex shows inhibition by deformation," Nature, 407:923-926, (2000).

Ito, T., "Interspecies transmission and receptor recognition of influenza A viruses," Microbiology and Immunology, 44:423-430, (2000).

Laube, B.L., "The expanding role of aerosols in systemic drug delivery, gene therapy, and vaccination," Respiratory Care, 50(9):1161-1176, (2005).

Le Calvez, H., et al., "Biochemical prevention and treatment of viral infections—a new paradigm in medicine for infectious diseases," Virology Journal, 1:12, (2004).

LeBlond, J., et al., "The serpin proteinase inhibitor 8: an endogenous furin inhibitor released from human platelets," Thrombosis and Haemostasis, 95:243-252, (2006).

Lee, M.K. and A.D. Lander, "Analysis of affinity and structural selectivity in the binding of proteins to glycosaminoglycans: development of a sensitive electrophoretic approach," Proceedings of the National Academy of Sciences of the United States of America, 88:2768-2772, (1991).

LiCalsi, C., et al., "A powder formulation of measles vaccine for aerosol delivery," Vaccine, 19(17-19):2629-2636, (2001).

Maa Y.F., et al., "Biopharmaceutical powders: particle formation and formulation considerations," Current Pharmaceutical Biotechnology, 1(3):283-302, (2000).

Maa Y.F., et al., "Protein inhalation powders: spray drying vs spray freeze drying," Pharmaceutical Research, 16(2):249-254, (1999).

Maa, Y.F., et al., "Spray-drying of air-liquid interface sensitive recombinant human growth hormone," Journal of Pharmaceutical Sciences, 87(2):152-159, (1998).

Malakhov, M.P., et al., "Sialidase fusion protein as a novel broad-spectrum inhibitor of influenza virus infection," Antimicrobial Agents and Chemotherapy, 1470-1479, (2006).

McKenna, B.J., et al., "Micrometer-sized spherical assemblies of polypeptides and small molecules by acid-base chemistry," Angewandte Chemie, 43(42):5652-5655, (2004).

*NexBio Featured by NIH News Article: New Drugs Against Flu—Seal off* (articlecanbefoundat:www3.niaid.nih.gov/news/focuson/flu/research/treatment/chen_newdrugs.htm) (accessed on Jun. 12, 2007) (2004).

NIH Grant No. 1U01AI070281-01; Development of Fludase as an Anti-Influenza Agent.

NIH Grant No. 2R44AI056786-03; Development of Fludase for Prevention of Influenza.

Oh, M. and C.A. Mirkin, M, "Chemically tailorable colloidal particles from infinite coordination polymers," Nature, 438(7068):651-654, (2005).

Pages THER-1 to THER-28 of The Merck Index, 12th Edition, Merck & Co. Rahway, N.J. (1996).

Pfutzner, A., et al., "Pilot study with technosphere/PTH(1-34)—a new approach for effective pulmonary delivery of parathyroid hormone (1-34)," Hormone and Metabolic Research, 35(5):319-323, (2003).

Potier, M., et al., "Fluorometric assay of neuraminidase with a sodium (4-methylumbelliferyl-alpha-D-N-acetylneuraminate) substrate," Analytical Biochemistry, 94:287-296, (1979).

Rahn and Schlenk, "Detection of aldehydes with 4-amino-5-hydrazino-1,2,4-triazole-3-thiol as spray reagent," Lipids, 8(11): 612-616, Nov. 1973.

Sellers, S.P., et al., "Dry powders of stable protein formulations from aqueous solutions prepared using supercritical CO(2)-assisted aerosolization," Journal of Pharmaceutical Sciences, 90(6):785-797, (2001).

Shak, S., et al., "Recombinant human DNase I reduces the viscosity of cystic fibrosis sputum," Proceedings of the National Academy of Sciences of the United States of America, 87:9188-9192 (1990).

Sinha, V.R., et al, "Biodegradable microspheres for protein delivery," Journal of Controlled Release, 90(3): 261-280, (2003).

Smyth, H. and A.J. Hickey, "Carriers in drug powder delivery. Implications for inhalation system design," American Journal of Drug Delivery, 3(2):117-132, (2005).

Sprecher, C.A., et al., "Molecular cloning, expression, and partial characterization of two novel members of the ovalbumin family of serine proteinase inhibitors," Journal of Biological Chemistry, 270:29854-29861, (1995).

Tashiro, M., et al., "Inhibitory effect of a protease inhibitor, leupeptin, on the development of influenza pneumonia, mediated by concomitant bacteria," Journal of General Virology, 68:2039-2043, (1987).

Taylor, G. and M. Gumbleton, "Aerosols for Macromolecule Delivery: Design Challenges and Solutions," American Journal of Drug Delivery, 2(3):143-155, (2004).

Vanbever, R, et al., "Formulation and physical characterization of large porous particles for inhalation," Pharmaceutical Research, 16(11):1735-1742, (1999).

Varki, A., "Selectins and other mammalian sialic acid-binding lectins," Current Opinion in Cell Biology, 4:257-266, (1992).

Weisgraber, K.H., et al., "Human apolipoprotein E. Determination of the heparin binding sites of apolipoprotein E3," Journal of Biological Chemistry, 261:2068-2076, (1986).

Witt, D.P and A.D. Lander, "Differential binding of chemokines to glycosaminoglycan subpopulations," Current Biology, 4:394-400, (1994).

Zhirnov, O.P., et al., "Cleavage of Influenza A Virus Hemagglutinin in Human Respiratory Epithelium Is Cell Associated and Sensitive to Exogenous Antiproteases," Journal of Virology, 76:8682-8689, (2002).

Zhirnov, O.P., et al., "Protective effect of protease inhibitors in influenza virus infected animals," Archives of Virology, 73:263-272, (1982).

Ben-Bassat et al., 'Processing of the Initiation Methionine from Proteins:Properties of the *Escherichia coli* Methionine Aminopeptidase and its Gene Structure', Journ of Bacteriology, 169(2):754-757, Feb. 1987.

(56) References Cited

OTHER PUBLICATIONS

Fiegel et al., 'Poly(Ether-Anhydride) Dry Powder Aerosols for Sustained Drug Delivery in the Lungs', Journ of Controlled Release, 96(3):411-423, May 18, 2004.
Larson, et al. 'Safety Evaluation of DAS181, A Sialidase Fusion Protein, in Rodents' Tox Sciences, 122(2):567-578, May 13, 2011.
International Search Report and Written Opinion issued in corresponding PCT application No. PCT/US2013/48729, dated Feb. 21, 2014 (7 pages).
Jovanovic et al., "Distinct effects of sucrose and trehalose on protein stability during supercritical fluid drying and freeze-drying," European Journal of Pharmaceutical Sciences, 2006, 27:336-345.
Qing et al., "RNA interference of influenza virus production by directly targeting mRNA for degradation and indirectly inhibiting all viral RNA transcription," Proc. Nat. Acad. Sci USA 2003, 100:2718-2723.
Bombuwala et al., "Colchitaxel, a coupled compound made from microtubule inhibitors colchicine and paclitaxel," J. Org. Chem, 2006, 2:13.
Hickey, "Carriers in Drug Powder Delivery: Implications for Inhalation System Design," American J. of Drug Delivery, 2005, 3(2): 117-132.
Chen et al., Influence of Histidine on the Stability and Physical Properties of a Fully Human Antibody in Aqueous and Solid Forms, Pharmaceutical Research, 2003, 20, pp. 1952-1960.
Extended European Search Report in European Application No. 13810800.6, dated Jul. 18, 2016, 6 pages.

* cited by examiner

SEQUENCE LISTING

```
<160> NUMBER OF SEQ ID NOS: 15

<210> SEQ ID NO 1
<211> LENGTH: 443
<212> TYPE: PRT
<213> ORGANISM: Artificial Sequence
<220> FEATURE:
<223> OTHER INFORMATION: Synthetic Construct

<400> SEQUENCE: 1

Val Lys Arg Lys Lys Lys Gly Gly Lys Asn Gly Lys Asn Arg Arg Asn
 1               5                  10                  15

Arg Lys Lys Lys Asn Pro Gly Asp His Pro Gln Ala Thr Pro Ala Pro
            20                  25                  30

Ala Pro Asp Ala Ser Thr Glu Leu Pro Ala Ser Met Ser Gln Ala Gln
        35                  40                  45

His Leu Ala Ala Asn Thr Ala Thr Asp Asn Tyr Arg Ile Pro Ala Ile
    50                  55                  60

Thr Thr Ala Pro Asn Gly Asp Leu Leu Ile Ser Tyr Asp Glu Arg Pro
65                  70                  75                  80

Lys Asp Asn Gly Asn Gly Gly Ser Asp Ala Pro Asn Pro Asn His Ile
                85                  90                  95

Val Gln Arg Arg Ser Thr Asp Gly Gly Lys Thr Trp Ser Ala Pro Thr
            100                 105                 110

Tyr Ile His Gln Gly Thr Glu Thr Gly Lys Lys Val Gly Tyr Ser Asp
        115                 120                 125

Pro Ser Tyr Val Val Asp His Gln Thr Gly Thr Ile Phe Asn Phe His
    130                 135                 140

Val Lys Ser Tyr Asp Gln Gly Trp Gly Gly Ser Arg Gly Gly Thr Asp
145                 150                 155                 160

Pro Glu Asn Arg Gly Ile Ile Gln Ala Glu Val Ser Thr Ser Thr Asp
                165                 170                 175

Asn Gly Trp Thr Trp Thr His Arg Thr Ile Thr Ala Asp Ile Thr Lys
            180                 185                 190

Asp Lys Pro Trp Thr Ala Arg Phe Ala Ala Ser Gly Gln Gly Ile Gln
        195                 200                 205
```

```
Ile Gln His Gly Pro His Ala Gly Arg Leu Val Gln Gln Tyr Thr Ile
    210                 215                 220

Arg Thr Ala Gly Gly Ala Val Gln Ala Val Ser Val Tyr Ser Asp Asp
225                 230                 235                 240

His Gly Lys Thr Trp Gln Ala Gly Thr Pro Ile Gly Thr Gly Met Asp
                245                 250                 255

Glu Asn Lys Val Val Glu Leu Ser Asp Gly Ser Leu Met Leu Asn Ser
            260                 265                 270

Arg Ala Ser Asp Gly Ser Gly Phe Arg Lys Val Ala His Ser Thr Asp
        275                 280                 285

Gly Gly Gln Thr Trp Ser Glu Pro Val Ser Asp Lys Asn Leu Pro Asp
    290                 295                 300

Ser Val Asp Asn Ala Gln Ile Ile Arg Ala Phe Pro Asn Ala Ala Pro
305                 310                 315                 320

Asp Asp Pro Arg Ala Lys Val Leu Leu Leu Ser His Ser Pro Asn Pro
                325                 330                 335

Arg Pro Trp Ser Arg Asp Arg Gly Thr Ile Ser Met Ser Cys Asp Asp
            340                 345                 350

Gly Ala Ser Trp Thr Thr Ser Lys Val Phe His Glu Pro Phe Val Gly
        355                 360                 365

Tyr Thr Thr Ile Ala Val Gln Ser Asp Gly Ser Ile Gly Leu Leu Ser
    370                 375                 380

Glu Asp Ala His Asn Gly Ala Asp Tyr Gly Gly Ile Trp Tyr Arg Asn
385                 390                 395                 400

Phe Thr Met Asn Trp Leu Gly Glu Gln Cys Gly Gln Lys Pro Ala Glu
                405                 410                 415

Gly Ala Asp Tyr Gly Gly Ile Trp Tyr Arg Asn Phe Thr Met Asn Trp
            420                 425                 430

Leu Gly Glu Gln Cys Gly Gln Lys Pro Ala Glu
        435                 440
```

<210> SEQ ID NO 2
<211> LENGTH: 444
<212> TYPE: PRT
<213> ORGANISM: Artificial Sequence
<220> FEATURE:
<223> OTHER INFORMATION: Synthetic Construct

<400> SEQUENCE: 2

```
Met Val Lys Arg Lys Lys Lys Gly Gly Lys Asn Gly Lys Asn Arg Arg
 1               5                  10                  15

Asn Arg Lys Lys Lys Asn Pro Gly Asp His Pro Gln Ala Thr Pro Ala
            20                  25                  30

Pro Ala Pro Asp Ala Ser Thr Glu Leu Pro Ala Ser Met Ser Gln Ala
        35                  40                  45

Gln His Leu Ala Ala Asn Thr Ala Thr Asp Asn Tyr Arg Ile Pro Ala
    50                  55                  60

Ile Thr Thr Ala Pro Asn Gly Asp Leu Leu Ile Ser Tyr Asp Glu Arg
65                  70                  75                  80

Pro Lys Asp Asn Gly Asn Gly Gly Ser Asp Ala Pro Asn Pro Asn His
                85                  90                  95

Ile Val Gln Arg Arg Ser Thr Asp Gly Gly Lys Thr Trp Ser Ala Pro
            100                 105                 110

Thr Tyr Ile His Gln Gly Thr Glu Thr Gly Lys Lys Val Gly Tyr Ser
        115                 120                 125
```

-continued

```
Asp Pro Ser Tyr Val Val Asp His Gln Thr Gly Thr Ile Phe Asn Phe
    130                 135                 140

His Val Lys Ser Tyr Asp Gln Gly Trp Gly Gly Ser Arg Gly Gly Thr
145                 150                 155                 160

Asp Pro Glu Asn Arg Gly Ile Ile Gln Ala Glu Val Ser Thr Ser Thr
                165                 170                 175

Asp Asn Gly Trp Thr Trp Thr His Arg Thr Ile Thr Ala Asp Ile Thr
            180                 185                 190

Lys Asp Lys Pro Trp Thr Ala Arg Phe Ala Ala Ser Gly Gln Gly Ile
        195                 200                 205

Gln Ile Gln His Gly Pro His Ala Gly Arg Leu Val Gln Gln Tyr Thr
    210                 215                 220

Ile Arg Thr Ala Gly Gly Ala Val Gln Ala Val Ser Val Tyr Ser Asp
225                 230                 235                 240

Asp His Gly Lys Thr Trp Gln Ala Gly Thr Pro Ile Gly Thr Gly Met
                245                 250                 255

Asp Glu Asn Lys Val Val Glu Leu Ser Asp Gly Ser Leu Met Leu Asn
            260                 265                 270

Ser Arg Ala Ser Asp Gly Ser Gly Phe Arg Lys Val Ala His Ser Thr
        275                 280                 285

Asp Gly Gly Gln Thr Trp Ser Glu Pro Val Ser Asp Lys Asn Leu Pro
    290                 295                 300

Asp Ser Val Asp Asn Ala Gln Ile Ile Arg Ala Phe Pro Asn Ala Ala
305                 310                 315                 320

Pro Asp Asp Pro Arg Ala Lys Val Leu Leu Leu Ser His Ser Pro Asn
                325                 330                 335

Pro Arg Pro Trp Ser Arg Asp Arg Gly Thr Ile Ser Met Ser Cys Asp
            340                 345                 350

Asp Gly Ala Ser Trp Thr Thr Ser Lys Val Phe His Glu Pro Phe Val
        355                 360                 365

Gly Tyr Thr Thr Ile Ala Val Gln Ser Asp Gly Ser Ile Gly Leu Leu
    370                 375                 380

Ser Glu Asp Ala His Asn Gly Ala Asp Tyr Gly Gly Ile Trp Tyr Arg
385                 390                 395                 400

Asn Phe Thr Met Asn Trp Leu Gly Glu Gln Cys Gly Gln Lys Pro Ala
                405                 410                 415

Glu Gly Ala Asp Tyr Gly Gly Ile Trp Tyr Arg Asn Phe Thr Met Asn
            420                 425                 430

Trp Leu Gly Glu Gln Cys Gly Gln Lys Pro Ala Glu
        435                 440


<210> SEQ ID NO 3
<211> LENGTH: 24
<212> TYPE: PRT
<213> ORGANISM: Homo sapiens

<400> SEQUENCE: 3

Asn Gly Arg Arg Ile Cys Leu Asp Leu Gln Ala Pro Leu Tyr Lys Lys
 1               5                  10                  15

Ile Ile Lys Lys Leu Leu Glu Ser
            20


<210> SEQ ID NO 4
<211> LENGTH: 27
<212> TYPE: PRT
<213> ORGANISM: Homo sapiens
```

<400> SEQUENCE: 4

Gly Arg Glu Leu Cys Leu Asp Pro Lys Glu Asn Trp Val Gln Arg Val
1 5 10 15

Val Glu Lys Phe Leu Lys Arg Ala Glu Asn Ser
20 25

<210> SEQ ID NO 5
<211> LENGTH: 34
<212> TYPE: PRT
<213> ORGANISM: Homo sapiens

<400> SEQUENCE: 5

Gln Ile His Phe Phe Phe Ala Lys Leu Asn Cys Arg Leu Tyr Arg Lys
1 5 10 15

Ala Asn Lys Ser Ser Lys Leu Val Ser Ala Asn Arg Leu Phe Gly Asp
20 25 30

Lys Ser

<210> SEQ ID NO 6
<211> LENGTH: 34
<212> TYPE: PRT
<213> ORGANISM: Homo sapiens

<400> SEQUENCE: 6

Glu Leu Arg Val Arg Leu Ala Ser His Leu Arg Lys Leu Arg Lys Arg
1 5 10 15

Leu Leu Arg Asp Ala Asp Asp Leu Gln Lys Arg Leu Ala Val Tyr Gln
20 25 30

Ala Gly

<210> SEQ ID NO 7
<211> LENGTH: 12
<212> TYPE: PRT
<213> ORGANISM: Homo sapiens

<400> SEQUENCE: 7

Arg Arg Leu Arg Arg Met Glu Ser Glu Ser Glu Ser
1 5 10

<210> SEQ ID NO 8
<211> LENGTH: 21
<212> TYPE: PRT
<213> ORGANISM: Homo sapiens

<400> SEQUENCE: 8

Lys Arg Lys Lys Lys Gly Gly Lys Asn Gly Lys Asn Thr Thr Asn Thr
1 5 10 15

Lys Lys Lys Asn Pro
20

<210> SEQ ID NO 9
<211> LENGTH: 415
<212> TYPE: PRT
<213> ORGANISM: Artificial Sequence
<220> FEATURE:
<223> OTHER INFORMATION: Synthetic Construct

<400> SEQUENCE: 9

Met Gly Asp His Pro Gln Ala Thr Pro Ala Pro Ala Pro Asp Ala Ser
1 5 10 15

```
Thr Glu Leu Pro Ala Ser Met Ser Gln Ala Gln His Leu Ala Ala Asn
            20                  25                  30

Thr Ala Thr Asp Asn Tyr Arg Ile Pro Ala Ile Thr Thr Ala Pro Asn
        35                  40                  45

Gly Asp Leu Leu Ile Ser Tyr Asp Glu Arg Pro Lys Asp Asn Gly Asn
    50                  55                  60

Gly Gly Ser Asp Ala Pro Asn Pro Asn His Ile Val Gln Arg Arg Ser
65                  70                  75                  80

Thr Asp Gly Gly Lys Thr Trp Ser Ala Pro Thr Tyr Ile His Gln Gly
                85                  90                  95

Thr Glu Thr Gly Lys Lys Val Gly Tyr Ser Asp Pro Ser Tyr Val Val
            100                 105                 110

Asp His Gln Thr Gly Thr Ile Phe Asn Phe His Val Lys Ser Tyr Asp
        115                 120                 125

Gln Gly Trp Gly Gly Ser Arg Gly Gly Thr Asp Pro Glu Asn Arg Gly
    130                 135                 140

Ile Ile Gln Ala Glu Val Ser Thr Ser Thr Asp Asn Gly Trp Thr Trp
145                 150                 155                 160

Thr His Arg Thr Ile Thr Ala Asp Ile Thr Lys Asp Lys Pro Trp Thr
                165                 170                 175

Ala Arg Phe Ala Ala Ser Gly Gln Gly Ile Gln Ile Gln His Gly Pro
            180                 185                 190

His Ala Gly Arg Leu Val Gln Gln Tyr Thr Ile Arg Thr Ala Gly Gly
        195                 200                 205

Ala Val Gln Ala Val Ser Val Tyr Ser Asp Asp His Gly Lys Thr Trp
    210                 215                 220

Gln Ala Gly Thr Pro Ile Gly Thr Gly Met Asp Glu Asn Lys Val Val
225                 230                 235                 240

Glu Leu Ser Asp Gly Ser Leu Met Leu Asn Ser Arg Ala Ser Asp Gly
                245                 250                 255

Ser Gly Phe Arg Lys Val Ala His Ser Thr Asp Gly Gly Gln Thr Trp
            260                 265                 270

Ser Glu Pro Val Ser Asp Lys Asn Leu Pro Asp Ser Val Asp Asn Ala
        275                 280                 285

Gln Ile Ile Arg Ala Phe Pro Asn Ala Ala Pro Asp Asp Pro Arg Ala
    290                 295                 300

Lys Val Leu Leu Leu Ser His Ser Pro Asn Pro Arg Pro Trp Ser Arg
305                 310                 315                 320

Asp Arg Gly Thr Ile Ser Met Ser Cys Asp Asp Gly Ala Ser Trp Thr
                325                 330                 335

Thr Ser Lys Val Phe His Glu Pro Phe Val Gly Tyr Thr Thr Ile Ala
            340                 345                 350

Val Gln Ser Asp Gly Ser Ile Gly Leu Leu Ser Glu Asp Ala His Asn
        355                 360                 365

Gly Ala Asp Tyr Gly Gly Ile Trp Tyr Arg Asn Phe Thr Met Asn Trp
    370                 375                 380

Leu Gly Glu Gln Cys Gly Gln Lys Pro Ala Lys Arg Lys Lys Lys Gly
385                 390                 395                 400

Gly Lys Asn Gly Lys Asn Arg Arg Asn Arg Lys Lys Lys Asn Pro
                405                 410                 415
```

<210> SEQ ID NO 10
<211> LENGTH: 430
<212> TYPE: PRT

```
<213> ORGANISM: Artificial Sequence
<220> FEATURE:
<223> OTHER INFORMATION: Synthetic Construct

<400> SEQUENCE: 10

Met Gly Asp His Pro Gln Ala Thr Pro Ala Pro Ala Pro Asp Ala Ser
1               5                   10                  15

Thr Glu Leu Pro Ala Ser Met Ser Gln Ala Gln His Leu Ala Ala Asn
            20                  25                  30

Thr Ala Thr Asp Asn Tyr Arg Ile Pro Ala Ile Thr Thr Ala Pro Asn
        35                  40                  45

Gly Asp Leu Leu Ile Ser Tyr Asp Glu Arg Pro Lys Asp Asn Gly Asn
    50                  55                  60

Gly Gly Ser Asp Ala Pro Asn Pro Asn His Ile Val Gln Arg Arg Ser
65                  70                  75                  80

Thr Asp Gly Gly Lys Thr Trp Ser Ala Pro Thr Tyr Ile His Gln Gly
                85                  90                  95

Thr Glu Thr Gly Lys Lys Val Gly Tyr Ser Asp Pro Ser Tyr Val Val
            100                 105                 110

Asp His Gln Thr Gly Thr Ile Phe Asn Phe His Val Lys Ser Tyr Asp
        115                 120                 125

Gln Gly Trp Gly Gly Ser Arg Gly Gly Thr Asp Pro Glu Asn Arg Gly
    130                 135                 140

Ile Ile Gln Ala Glu Val Ser Thr Ser Thr Asp Asn Gly Trp Thr Trp
145                 150                 155                 160

Thr His Arg Thr Ile Thr Ala Asp Ile Thr Lys Asp Lys Pro Trp Thr
                165                 170                 175

Ala Arg Phe Ala Ala Ser Gly Gln Gly Ile Gln Ile Gln His Gly Pro
            180                 185                 190

His Ala Gly Arg Leu Val Gln Gln Tyr Thr Ile Arg Thr Ala Gly Gly
        195                 200                 205

Ala Val Gln Ala Val Ser Val Tyr Ser Asp Asp His Gly Lys Thr Trp
    210                 215                 220

Gln Ala Gly Thr Pro Ile Gly Thr Gly Met Asp Glu Asn Lys Val Val
225                 230                 235                 240

Glu Leu Ser Asp Gly Ser Leu Met Leu Asn Ser Arg Ala Ser Asp Gly
                245                 250                 255

Ser Gly Phe Arg Lys Val Ala His Ser Thr Asp Gly Gly Gln Thr Trp
            260                 265                 270

Ser Glu Pro Val Ser Asp Lys Asn Leu Pro Asp Ser Val Asp Asn Ala
        275                 280                 285

Gln Ile Ile Arg Ala Phe Pro Asn Ala Ala Pro Asp Asp Pro Arg Ala
    290                 295                 300

Lys Val Leu Leu Leu Ser His Ser Pro Asn Pro Arg Pro Trp Ser Arg
305                 310                 315                 320

Asp Arg Gly Thr Ile Ser Met Ser Cys Asp Asp Gly Ala Ser Trp Thr
                325                 330                 335

Thr Ser Lys Val Phe His Glu Pro Phe Val Gly Tyr Thr Thr Ile Ala
            340                 345                 350

Val Gln Ser Asp Gly Ser Ile Gly Leu Leu Ser Glu Asp Ala His Asn
        355                 360                 365

Gly Ala Asp Tyr Gly Gly Ile Trp Tyr Arg Asn Phe Thr Met Asn Trp
    370                 375                 380

Leu Gly Glu Gln Cys Gly Gln Lys Pro Ala Glu Pro Ser Pro Ala Pro
```

385 390 395 400

Ser Pro Thr Ala Ala Pro Ser Ala Ala Lys Arg Lys Lys Lys Gly Gly
405 410 415

Lys Asn Gly Lys Asn Arg Arg Asn Arg Lys Lys Lys Asn Pro
420 425 430

<210> SEQ ID NO 11
<211> LENGTH: 400
<212> TYPE: PRT
<213> ORGANISM: Artificial Sequence
<220> FEATURE:
<223> OTHER INFORMATION: Synthetic Construct

<400> SEQUENCE: 11

Met Gly Glu Leu Pro Ala Ser Met Ser Gln Ala Gln His Leu Ala Ala
1 5 10 15

Asn Thr Ala Thr Asp Asn Tyr Arg Ile Pro Ala Ile Thr Thr Ala Pro
20 25 30

Asn Gly Asp Leu Leu Ile Ser Tyr Asp Glu Arg Pro Lys Asp Asn Gly
35 40 45

Asn Gly Gly Ser Asp Ala Pro Asn Pro Asn His Ile Val Gln Arg Arg
50 55 60

Ser Thr Asp Gly Gly Lys Thr Trp Ser Ala Pro Thr Tyr Ile His Gln
65 70 75 80

Gly Thr Glu Thr Gly Lys Lys Val Gly Tyr Ser Asp Pro Ser Tyr Val
85 90 95

Val Asp His Gln Thr Gly Thr Ile Phe Asn Phe His Val Lys Ser Tyr
100 105 110

Asp Gln Gly Trp Gly Gly Ser Arg Gly Gly Thr Asp Pro Glu Asn Arg
115 120 125

Gly Ile Ile Gln Ala Glu Val Ser Thr Ser Thr Asp Asn Gly Trp Thr
130 135 140

Trp Thr His Arg Thr Ile Thr Ala Asp Ile Thr Lys Asp Lys Pro Trp
145 150 155 160

Thr Ala Arg Phe Ala Ala Ser Gly Gln Gly Ile Gln Ile Gln His Gly
165 170 175

Pro His Ala Gly Arg Leu Val Gln Gln Tyr Thr Ile Arg Thr Ala Gly
180 185 190

Gly Ala Val Gln Ala Val Ser Val Tyr Ser Asp Asp His Gly Lys Thr
195 200 205

Trp Gln Ala Gly Thr Pro Ile Gly Thr Gly Met Asp Glu Asn Lys Val
210 215 220

Val Glu Leu Ser Asp Gly Ser Leu Met Leu Asn Ser Arg Ala Ser Asp
225 230 235 240

Gly Ser Gly Phe Arg Lys Val Ala His Ser Thr Asp Gly Gly Gln Thr
245 250 255

Trp Ser Glu Pro Val Ser Asp Lys Asn Leu Pro Asp Ser Val Asp Asn
260 265 270

Ala Gln Ile Ile Arg Ala Phe Pro Asn Ala Ala Pro Asp Asp Pro Arg
275 280 285

Ala Lys Val Leu Leu Leu Ser His Ser Pro Asn Pro Arg Pro Trp Ser
290 295 300

Arg Asp Arg Gly Thr Ile Ser Met Ser Cys Asp Asp Gly Ala Ser Trp
305 310 315 320

Thr Thr Ser Lys Val Phe His Glu Pro Phe Val Gly Tyr Thr Thr Ile 325 330 335

Ala Val Gln Ser Asp Gly Ser Ile Gly Leu Leu Ser Glu Asp Ala His
340 345 350

Asn Gly Ala Asp Tyr Gly Gly Ile Trp Tyr Arg Asn Phe Thr Met Asn
355 360 365

Trp Leu Gly Glu Gln Cys Gly Gln Lys Pro Ala Lys Arg Lys Lys Lys
370 375 380

Gly Gly Lys Asn Gly Lys Asn Arg Arg Asn Arg Lys Lys Lys Asn Pro
385 390 395 400

<210> SEQ ID NO 12
<211> LENGTH: 415
<212> TYPE: PRT
<213> ORGANISM: Artificial Sequence
<220> FEATURE:
<223> OTHER INFORMATION: Synthetic Construct

<400> SEQUENCE: 12

Met Gly Glu Leu Pro Ala Ser Met Ser Gln Ala Gln His Leu Ala Ala
1 5 10 15

Asn Thr Ala Thr Asp Asn Tyr Arg Ile Pro Ala Ile Thr Thr Ala Pro
20 25 30

Asn Gly Asp Leu Leu Ile Ser Tyr Asp Glu Arg Pro Lys Asp Asn Gly
35 40 45

Asn Gly Gly Ser Asp Ala Pro Asn Pro Asn His Ile Val Gln Arg Arg
50 55 60

Ser Thr Asp Gly Gly Lys Thr Trp Ser Ala Pro Thr Tyr Ile His Gln
65 70 75 80

Gly Thr Glu Thr Gly Lys Lys Val Gly Tyr Ser Asp Pro Ser Tyr Val
85 90 95

Val Asp His Gln Thr Gly Thr Ile Phe Asn Phe His Val Lys Ser Tyr
100 105 110

Asp Gln Gly Trp Gly Gly Ser Arg Gly Gly Thr Asp Pro Glu Asn Arg
115 120 125

Gly Ile Ile Gln Ala Glu Val Ser Thr Ser Thr Asp Asn Gly Trp Thr
130 135 140

Trp Thr His Arg Thr Ile Thr Ala Asp Ile Thr Lys Asp Lys Pro Trp
145 150 155 160

Thr Ala Arg Phe Ala Ala Ser Gly Gln Gly Ile Gln Ile Gln His Gly
165 170 175

Pro His Ala Gly Arg Leu Val Gln Gln Tyr Thr Ile Arg Thr Ala Gly
180 185 190

Gly Ala Val Gln Ala Val Ser Val Tyr Ser Asp Asp His Gly Lys Thr
195 200 205

Trp Gln Ala Gly Thr Pro Ile Gly Thr Gly Met Asp Glu Asn Lys Val
210 215 220

Val Glu Leu Ser Asp Gly Ser Leu Met Leu Asn Ser Arg Ala Ser Asp
225 230 235 240

Gly Ser Gly Phe Arg Lys Val Ala His Ser Thr Asp Gly Gly Gln Thr
245 250 255

Trp Ser Glu Pro Val Ser Asp Lys Asn Leu Pro Asp Ser Val Asp Asn
260 265 270

Ala Gln Ile Ile Arg Ala Phe Pro Asn Ala Ala Pro Asp Asp Pro Arg
275 280 285

Ala Lys Val Leu Leu Leu Ser His Ser Pro Asn Pro Arg Pro Trp Ser

```
    290                 295                 300

Arg Asp Arg Gly Thr Ile Ser Met Ser Cys Asp Asp Gly Ala Ser Trp
305                 310                 315                 320

Thr Thr Ser Lys Val Phe His Glu Pro Phe Val Gly Tyr Thr Thr Ile
                325                 330                 335

Ala Val Gln Ser Asp Gly Ser Ile Gly Leu Leu Ser Glu Asp Ala His
            340                 345                 350

Asn Gly Ala Asp Tyr Gly Gly Ile Trp Tyr Arg Asn Phe Thr Met Asn
        355                 360                 365

Trp Leu Gly Glu Gln Cys Gly Gln Lys Pro Ala Glu Pro Ser Pro Ala
    370                 375                 380

Pro Ser Pro Thr Ala Ala Pro Ser Ala Ala Lys Arg Lys Lys Lys Gly
385                 390                 395                 400

Gly Lys Asn Gly Lys Asn Arg Arg Asn Arg Lys Lys Lys Asn Pro
                405                 410                 415


<210> SEQ ID NO 13
<211> LENGTH: 422
<212> TYPE: PRT
<213> ORGANISM: Artificial Sequence
<220> FEATURE:
<223> OTHER INFORMATION: Synthetic Construct

<400> SEQUENCE: 13

Met Val Lys Arg Lys Lys Lys Gly Gly Lys Asn Gly Lys Asn Arg Arg
 1               5                  10                  15

Asn Arg Lys Lys Lys Asn Pro Gly Gly Gly Gly Ser Gly Asp His Pro
            20                  25                  30

Gln Ala Thr Pro Ala Pro Ala Pro Asp Ala Ser Thr Glu Leu Pro Ala
        35                  40                  45

Ser Met Ser Gln Ala Gln His Leu Ala Ala Asn Thr Ala Thr Asp Asn
    50                  55                  60

Tyr Arg Ile Pro Ala Ile Thr Thr Ala Pro Asn Gly Asp Leu Leu Ile
65                  70                  75                  80

Ser Tyr Asp Glu Arg Pro Lys Asp Asn Gly Asn Gly Gly Ser Asp Ala
                85                  90                  95

Pro Asn Pro Asn His Ile Val Gln Arg Arg Ser Thr Asp Gly Gly Lys
            100                 105                 110

Thr Trp Ser Ala Pro Thr Tyr Ile His Gln Gly Thr Glu Thr Gly Lys
        115                 120                 125

Lys Val Gly Tyr Ser Asp Pro Ser Tyr Val Val Asp His Gln Thr Gly
    130                 135                 140

Thr Ile Phe Asn Phe His Val Lys Ser Tyr Asp Gln Gly Trp Gly Gly
145                 150                 155                 160

Ser Arg Gly Gly Thr Asp Pro Glu Asn Arg Gly Ile Ile Gln Ala Glu
                165                 170                 175

Val Ser Thr Ser Thr Asp Asn Gly Trp Thr Trp Thr His Arg Thr Ile
            180                 185                 190

Thr Ala Asp Ile Thr Lys Asp Lys Pro Trp Thr Ala Arg Phe Ala Ala
        195                 200                 205

Ser Gly Gln Gly Ile Gln Ile Gln His Gly Pro His Ala Gly Arg Leu
    210                 215                 220

Val Gln Gln Tyr Thr Ile Arg Thr Ala Gly Gly Ala Val Gln Ala Val
225                 230                 235                 240

Ser Val Tyr Ser Asp Asp His Gly Lys Thr Trp Gln Ala Gly Thr Pro
```

-continued

```
                245                 250                 255

Ile Gly Thr Gly Met Asp Glu Asn Lys Val Val Glu Leu Ser Asp Gly
            260                 265                 270

Ser Leu Met Leu Asn Ser Arg Ala Ser Asp Gly Ser Gly Phe Arg Lys
        275                 280                 285

Val Ala His Ser Thr Asp Gly Gly Gln Thr Trp Ser Glu Pro Val Ser
    290                 295                 300

Asp Lys Asn Leu Pro Asp Ser Val Asp Asn Ala Gln Ile Ile Arg Ala
305                 310                 315                 320

Phe Pro Asn Ala Ala Pro Asp Asp Pro Arg Ala Lys Val Leu Leu Leu
                325                 330                 335

Ser His Ser Pro Asn Pro Arg Pro Trp Ser Arg Asp Arg Gly Thr Ile
            340                 345                 350

Ser Met Ser Cys Asp Asp Gly Ala Ser Trp Thr Thr Ser Lys Val Phe
        355                 360                 365

His Glu Pro Phe Val Gly Tyr Thr Thr Ile Ala Val Gln Ser Asp Gly
    370                 375                 380

Ser Ile Gly Leu Leu Ser Glu Asp Ala His Asn Gly Ala Asp Tyr Gly
385                 390                 395                 400

Gly Ile Trp Tyr Arg Asn Phe Thr Met Asn Trp Leu Gly Glu Gln Cys
                405                 410                 415

Gly Gln Lys Pro Ala Glu
            420


<210> SEQ ID NO 14
<211> LENGTH: 901
<212> TYPE: PRT
<213> ORGANISM: Actinomyces viscosus

<400> SEQUENCE: 14

Met Thr Ser His Ser Pro Phe Ser Arg Arg Arg Leu Pro Ala Leu Leu
 1               5                  10                  15

Gly Ser Leu Pro Leu Ala Ala Thr Gly Leu Ile Ala Ala Ala Pro Pro
            20                  25                  30

Ala His Ala Val Pro Thr Ser Asp Gly Leu Ala Asp Val Thr Ile Thr
        35                  40                  45

Gln Val Asn Ala Pro Ala Asp Gly Leu Tyr Ser Val Gly Asp Val Met
    50                  55                  60

Thr Phe Asn Ile Thr Leu Thr Asn Thr Ser Gly Glu Ala His Ser Tyr
65                  70                  75                  80

Ala Pro Ala Ser Thr Asn Leu Ser Gly Asn Val Ser Lys Cys Arg Trp
                85                  90                  95

Arg Asn Val Pro Ala Gly Thr Thr Lys Thr Asp Cys Thr Gly Leu Ala
            100                 105                 110

Thr His Thr Val Thr Ala Glu Asp Leu Lys Ala Gly Gly Phe Thr Pro
        115                 120                 125

Gln Ile Ala Tyr Glu Val Lys Ala Val Glu Tyr Ala Gly Lys Ala Leu
    130                 135                 140

Ser Thr Pro Glu Thr Ile Lys Gly Ala Thr Ser Pro Val Lys Ala Asn
145                 150                 155                 160

Ser Leu Arg Val Glu Ser Ile Thr Pro Ser Ser Ser Gln Glu Asn Tyr
                165                 170                 175

Lys Leu Gly Asp Thr Val Ser Tyr Thr Val Arg Val Arg Ser Val Ser
            180                 185                 190
```

-continued

```
Asp Lys Thr Ile Asn Val Ala Ala Thr Glu Ser Ser Phe Asp Asp Leu
        195                 200                 205

Gly Arg Gln Cys His Trp Gly Gly Leu Lys Pro Gly Lys Gly Ala Val
    210                 215                 220

Tyr Asn Cys Lys Pro Leu Thr His Thr Ile Thr Gln Ala Asp Val Asp
225                 230                 235                 240

Ala Gly Arg Trp Thr Pro Ser Ile Thr Leu Thr Ala Thr Gly Thr Asp
                245                 250                 255

Gly Ala Thr Leu Gln Thr Leu Thr Ala Thr Gly Asn Pro Ile Asn Val
            260                 265                 270

Val Gly Asp His Pro Gln Ala Thr Pro Ala Pro Ala Pro Asp Ala Ser
        275                 280                 285

Thr Glu Leu Pro Ala Ser Met Ser Gln Ala Gln His Leu Ala Ala Asn
    290                 295                 300

Thr Ala Thr Asp Asn Tyr Arg Ile Pro Ala Ile Thr Thr Ala Pro Asn
305                 310                 315                 320

Gly Asp Leu Leu Ile Ser Tyr Asp Glu Arg Pro Lys Asp Asn Gly Asn
                325                 330                 335

Gly Gly Ser Asp Ala Pro Asn Pro Asn His Ile Val Gln Arg Arg Ser
            340                 345                 350

Thr Asp Gly Gly Lys Thr Trp Ser Ala Pro Thr Tyr Ile His Gln Gly
        355                 360                 365

Thr Glu Thr Gly Lys Lys Val Gly Tyr Ser Asp Pro Ser Tyr Val Val
    370                 375                 380

Asp His Gln Thr Gly Thr Ile Phe Asn Phe His Val Lys Ser Tyr Asp
385                 390                 395                 400

Gln Gly Trp Gly Gly Ser Arg Gly Gly Thr Asp Pro Glu Asn Arg Gly
                405                 410                 415

Ile Ile Gln Ala Glu Val Ser Thr Ser Thr Asp Asn Gly Trp Thr Trp
            420                 425                 430

Thr His Arg Thr Ile Thr Ala Asp Ile Thr Lys Asp Lys Pro Trp Thr
        435                 440                 445

Ala Arg Phe Ala Ala Ser Gly Gln Gly Ile Gln Ile Gln His Gly Pro
    450                 455                 460

His Ala Gly Arg Leu Val Gln Gln Tyr Thr Ile Arg Thr Ala Gly Gly
465                 470                 475                 480

Ala Val Gln Ala Val Ser Val Tyr Ser Asp Asp His Gly Lys Thr Trp
                485                 490                 495

Gln Ala Gly Thr Pro Ile Gly Thr Gly Met Asp Glu Asn Lys Val Val
            500                 505                 510

Glu Leu Ser Asp Gly Ser Leu Met Leu Asn Ser Arg Ala Ser Asp Gly
        515                 520                 525

Ser Gly Phe Arg Lys Val Ala His Ser Thr Asp Gly Gly Gln Thr Trp
    530                 535                 540

Ser Glu Pro Val Ser Asp Lys Asn Leu Pro Asp Ser Val Asp Asn Ala
545                 550                 555                 560

Gln Ile Ile Arg Ala Phe Pro Asn Ala Ala Pro Asp Asp Pro Arg Ala
                565                 570                 575

Lys Val Leu Leu Leu Ser His Ser Pro Asn Pro Arg Pro Trp Ser Arg
            580                 585                 590

Asp Arg Gly Thr Ile Ser Met Ser Cys Asp Asp Gly Ala Ser Trp Thr
        595                 600                 605

Thr Ser Lys Val Phe His Glu Pro Phe Val Gly Tyr Thr Thr Ile Ala
```

-continued

```
    610                 615                 620

Val Gln Ser Asp Gly Ser Ile Gly Leu Leu Ser Glu Asp Ala His Asn
625                 630                 635                 640

Gly Ala Asp Tyr Gly Gly Ile Trp Tyr Arg Asn Phe Thr Met Asn Trp
                645                 650                 655

Leu Gly Glu Gln Cys Gly Gln Lys Pro Ala Glu Pro Ser Pro Ala Pro
            660                 665                 670

Ser Pro Thr Ala Ala Pro Ser Ala Ala Pro Thr Glu Lys Pro Ala Pro
        675                 680                 685

Ser Ala Ala Pro Ser Ala Glu Pro Thr Gln Ala Pro Ala Pro Ser Ser
    690                 695                 700

Ala Pro Glu Pro Ser Ala Ala Pro Glu Pro Ser Ser Ala Pro Ala Pro
705                 710                 715                 720

Glu Pro Thr Thr Ala Pro Ser Thr Glu Pro Thr Pro Ala Pro Ala Pro
                725                 730                 735

Ser Ser Ala Pro Glu Gln Thr Asp Gly Pro Thr Ala Ala Pro Ala Pro
            740                 745                 750

Glu Thr Ser Ser Ala Pro Ala Ala Glu Pro Thr Gln Ala Pro Thr Val
        755                 760                 765

Ala Pro Ser Val Glu Pro Thr Gln Ala Pro Gly Ala Gln Pro Ser Ser
    770                 775                 780

Ala Pro Lys Pro Gly Ala Thr Gly Arg Ala Pro Ser Val Val Asn Pro
785                 790                 795                 800

Lys Ala Thr Gly Ala Ala Thr Glu Pro Gly Thr Pro Ser Ser Ser Ala
                805                 810                 815

Ser Pro Ala Pro Ser Arg Asn Ala Ala Pro Thr Pro Lys Pro Gly Met
            820                 825                 830

Glu Pro Asp Glu Ile Asp Arg Pro Ser Asp Gly Thr Met Ala Gln Pro
        835                 840                 845

Thr Gly Gly Ala Ser Ala Pro Ser Ala Ala Pro Thr Gln Ala Ala Lys
    850                 855                 860

Ala Gly Ser Arg Leu Ser Arg Thr Gly Thr Asn Ala Leu Leu Ile Leu
865                 870                 875                 880

Gly Leu Ala Gly Val Ala Val Val Gly Gly Tyr Leu Leu Leu Arg Ala
                885                 890                 895

Arg Arg Ser Lys Asn
            900


<210> SEQ ID NO 15
<211> LENGTH: 394
<212> TYPE: PRT
<213> ORGANISM: Actinomyces viscosus

<400> SEQUENCE: 15

Gly Asp His Pro Gln Ala Thr Pro Ala Pro Ala Pro Asp Ala Ser Thr
 1               5                  10                  15

Glu Leu Pro Ala Ser Met Ser Gln Ala Gln His Leu Ala Ala Asn Thr
            20                  25                  30

Ala Thr Asp Asn Tyr Arg Ile Pro Ala Ile Thr Thr Ala Pro Asn Gly
        35                  40                  45

Asp Leu Leu Ile Ser Tyr Asp Glu Arg Pro Lys Asp Asn Gly Asn Gly
    50                  55                  60

Gly Ser Asp Ala Pro Asn Pro Asn His Ile Val Gln Arg Arg Ser Thr
65                  70                  75                  80
```

-continued

```
Asp Gly Gly Lys Thr Trp Ser Ala Pro Thr Tyr Ile His Gln Gly Thr
                85                  90                  95

Glu Thr Gly Lys Lys Val Gly Tyr Ser Asp Pro Ser Tyr Val Val Asp
            100                 105                 110

His Gln Thr Gly Thr Ile Phe Asn Phe His Val Lys Ser Tyr Asp Gln
        115                 120                 125

Gly Trp Gly Gly Ser Arg Gly Gly Thr Asp Pro Glu Asn Arg Gly Ile
    130                 135                 140

Ile Gln Ala Glu Val Ser Thr Ser Thr Asp Asn Gly Trp Thr Trp Thr
145                 150                 155                 160

His Arg Thr Ile Thr Ala Asp Ile Thr Lys Asp Lys Pro Trp Thr Ala
                165                 170                 175

Arg Phe Ala Ala Ser Gly Gln Gly Ile Gln Ile Gln His Gly Pro His
            180                 185                 190

Ala Gly Arg Leu Val Gln Gln Tyr Thr Ile Arg Thr Ala Gly Gly Ala
        195                 200                 205

Val Gln Ala Val Ser Val Tyr Ser Asp Asp His Gly Lys Thr Trp Gln
    210                 215                 220

Ala Gly Thr Pro Ile Gly Thr Gly Met Asp Glu Asn Lys Val Val Glu
225                 230                 235                 240

Leu Ser Asp Gly Ser Leu Met Leu Asn Ser Arg Ala Ser Asp Gly Ser
                245                 250                 255

Gly Phe Arg Lys Val Ala His Ser Thr Asp Gly Gly Gln Thr Trp Ser
            260                 265                 270

Glu Pro Val Ser Asp Lys Asn Leu Pro Asp Ser Val Asp Asn Ala Gln
        275                 280                 285

Ile Ile Arg Ala Phe Pro Asn Ala Ala Pro Asp Asp Pro Arg Ala Lys
    290                 295                 300

Val Leu Leu Leu Ser His Ser Pro Asn Pro Arg Pro Trp Ser Arg Asp
305                 310                 315                 320

Arg Gly Thr Ile Ser Met Ser Cys Asp Asp Gly Ala Ser Trp Thr Thr
                325                 330                 335

Ser Lys Val Phe His Glu Pro Phe Val Gly Tyr Thr Thr Ile Ala Val
            340                 345                 350

Gln Ser Asp Gly Ser Ile Gly Leu Leu Ser Glu Asp Ala His Asn Gly
        355                 360                 365

Ala Asp Tyr Gly Gly Ile Trp Tyr Arg Asn Phe Thr Met Asn Trp Leu
    370                 375                 380

Gly Glu Gln Cys Gly Gln Lys Pro Ala Glu
385                 390
```

MICROPARTICLE FORMULATIONS FOR DELIVERY TO THE LOWER AND CENTRAL RESPIRATORY TRACT AND METHODS OF MANUFACTURE

RELATED APPLICATIONS

This application claims priority to U.S. application Ser. No. 13/931,419, filed Jun. 28, 2013, which claims priority to U.S. Provisional Application Ser. No. 61/665,807, filed Jun. 28, 2012 and U.S. Provisional Application Ser. No. 61/779,653, filed Mar. 13, 2013.

FEDERALLY SPONSORED RESEARCH OR DEVELOPMENT

This invention was made with Government support under Grant No. 5R43A1056786 awarded by the Department of Health and Human Services, National Institutes of Health. The Government has certain rights in this invention.

BACKGROUND

The preparation and delivery of active agents including small molecules and biologics (e.g., proteins, carbohydrates, nucleic acids, hormones, lipids) in powder or microparticle form is an area of concentrated research and development activity in a variety of applications including pharmaceuticals (where the active agent is an Active Pharmaceutical Ingredient (API)), nutraceuticals and cosmetics. In many cases it is desirable for the microparticles to have a predetermined, relatively uniform size because size can impact the deposition of the microparticles and release of the API.

In the case of inhalable microparticle formulations it is particularly important that microparticle size be controlled so that the API can be delivered to the appropriate region(s) of the respiratory tract. Examples of diseases that can be treated by delivery of a pharmaceutical formulation to the upper and/or central respiratory tract include respiratory tract infections (RTIs) such as influenza, parainfluenza, RSV, sinusitis, otitis, laryngitis, bronchitis and pneumonia. In addition, there are large numbers of respiratory tract disorders (RTDs) that may not be caused by an infectious pathogen but affect the upper and central respiratory tract; such disorders, which can have a genetic basis, arise due to immunodeficiencies or other (e.g., α-1-antitrypsin) deficiencies, result from exposure to allergens and/or chemical pollutants, or present as complications of infectious diseases such as the RTIs described above or inflammatory diseases such as inflammatory bowel syndrome and Crohn's disease include allergic and non-allergic asthma, COPD, bronchiectasis, vasculitis, mucous plugging, Wegener's granulomatosis and cystic fibrosis (CF).

In some cases, for example, when an infection is present in the lower respiratory tract, it can be desirable to administer a formulation containing microparticles that are delivered to the lower and central respiratory tract. Thus, in some cases it can be desirable to administer a formulation containing microparticles that have an MMAD of 3-8 microns or 5-7 microns. The smaller MMAD of the microparticles in such formulations can increase the fraction of microparticles that are small enough to become absorbed into the bloodstream. Since systemic exposure is sometimes not desirable, the formulations with a relatively small MMAD can pose increase risk of unwanted systemic exposure. However, tight control over the range of the particle size can reduce the risk. Moreover, for some patients, e.g., immunocompromised patients, suffering from influenza or parainfluenza, the importance of delivering therapy to the lower respiratory tract justifies a potential increase in risk of a small degree of systemic exposure.

For the treatment of RTIs and RTDs, the microparticles of the drug must be small enough to be deposited and act at the desired target site in the upper and/or central respiratory airways of the lungs (e.g., the epithelial cells of the upper respiratory tract in the case of influenza; the central respiratory tract in the case of asthma or COPD), yet not be so small as to reach deeper parts of the lungs, such as the alveoli, become absorbed into the bloodstream, and compromise the pharmacokinetic profile or even the safety of the drug. Accordingly, there is a need for a method of producing microparticle formulations whose size can be fine-tuned for delivery to a target site of interest while reducing delivery to sites that are undesirable.

There further is a need for microparticle formulations in which the incorporated active agent is stable for relatively long periods of time. For stability, the active agent in the formulation should not react with or otherwise be degraded by other ingredients/excipients in the formulation (for example, compounds that improve bioavailability, delivery, safety, etc. of the active agent). The active agent in the formulation should also be protected from components that may be present in the packaging materials and/or delivery systems, e.g., medical devices, containers, capsules or gels. For example, when the active agent is a protein, aldehydes and other cross-linking agents that may be present in some packaging materials or arise as byproducts during the manufacture of the materials can react with the active agent to form protein aggregates or oligomers. There is a need for microparticle formulations that can protect the active agent against components of packaging materials that could compromise its stability.

SUMMARY

Provided herein are methods of producing relatively uniform sized microparticle formulations of a macromolecule or small molecule active agent. In some cases, the resulting microparticles are of a predetermined size and have a narrow range of size distribution (geometric standard deviation ("GSD") between 1.2-2.0, e.g., 1.5-1.7). The methods provided herein include the steps of mixing together a solution of an active agent in an aqueous solvent, a counterion and a solvent (e.g., isopropanol) and cooling the resulting mixture (also referred to herein as cocktail solution or feedstock solution) to a predetermined temperature below about 25° C. at a cooling rate that is maintained at a constant fixed value until the mixture is at a predetermined temperature below about 25° C. In many cases there are two or more cooling phases during which the temperate is decreased at a fixed rate. In some cases the solution is held for a period of time at a predetermined temperature. The resulting microparticles can be separated from the mixture to remove components other than the microparticles by, for example, sedimentation, filtration and/or freeze-drying.

The size of the microparticles of the resulting formulations is controlled, in large part, by a combination of the choice of counterion and the cooling rate. In general, the faster the cooling rate, the smaller the size of the resulting microparticles. The uniformity of the size is achieved in certain cases by maintaining the cooling rate at a constant, fixed value until the mixture is cooled to the desired predetermined temperature below about 25° C. Thus, the cooling rate is maintained regardless of the changing temperature differential during cooling, i.e., the difference between the temperature of the cocktail solution at any given time during the cooling process and the final predetermined temperature to which it is cooled.

In general, in the case of the sialidase fusion protein DAS181, whose sequence is set forth in SEQ ID NO:1 (no amino terminal methoionine) and SEQ ID NO:2 (amino terminal methionine present), when the methods employ faster cooling rates and counterions such as sodium sulfate or magnesium sulfate, smaller microparticles (value between about 3 microns to about 8 microns mass median aerodynamic diameter (MMAD)) of DAS181 are formed.

In particular embodiments, provided herein are methods of making uniform microparticle formulations of DAS181 with a mass median aerodynamic diameter (MMAD) that has a value between about 8.0 microns to about 3.0 microns (preferably 7.5-4.5 microns) and a geometric standard deviation (GSD) of between about 1.2 to about 2.0 (e.g., 1.5-1.7). As discussed further below, in some cases it is desirable that microparticles of DAS181 or other active agents for delivering microparticles to the central and lower respiratory tract for treating respiratory tract infections or disorders such as influenza, parainfluenza, asthma or COPD have a size, generally 4 microns to 10 microns, which permits their deposition at locations that are the targets of the disease, such as the throat, trachea and bronchi, while reducing deposition in the deep lung, e.g., alveoli and/or absorption into the blood stream. In many cases, the site of deposition depends on the inhaler flow rate. In some embodiments the particles are inhaled at 50-70 l/min (e.g., 55-65 l/min or 60 l/min).

In some embodiments, the methods provided herein include citric acid or citrate as the counterion and a constant fixed cooling rate of between about 0.3° C./min to about 0.8° C./min to cool the feedstock solution from a temperature of about 25° C. to a predetermined temperature of about −45° C., −50° C., −55° C., or −60° C., whereby a microparticle formulation of DAS181 that has a particle size (MMAD) of about 6.0, 6.1, 6.2, 6.3, 6.4, 6.5, 6.6, 6.7, 6.8, 6.9 or 7.0 microns and a GSD of about 1.2-2.0 is formed.

In one embodiment, a uniform formulation of DAS181 microparticles of mass median aerodynamic diameter (MMAD) about 6.0, 6.1, 6.2, 6.3, 6.4, 6.5, 6.6, 6.7, 6.8, 6.9 or 7.0 microns and a GSD of 1.5-1.7 is prepared by cooling a cocktail solution comprising DAS181 as the active agent, magnesium sulfate as a counterion and isopropanol as the organic solvent from a temperature of about 25° C. to a temperature of −45° C. at a cooling rate of −0.5° C./min.

Also provided are microparticle formulations prepared according to the methods provided herein. In some embodiments, the active agent or API in the formulation is for treating diseases that affect the respiratory tract such as influenza, asthma and COPD.

An example of an API that can be used to treat respiratory diseases and disorders is the sialidase fusion protein, DAS181. The DAS181 fusion protein can be expressed by various expression systems. As a result, it can be present and functional in the two forms: one in which the polypeptide begins with a methionine (SEQ ID NO:2) or one in which the polypeptide lacks the initial methionine and begins with valine (SEQ ID NO:1). Hence, in an example where the API is DAS181, the API component can be the polypeptide of SEQ ID NO:1 or the polypeptide of SEQ ID NO:2 or it can be a combination comprising the polypeptide of SEQ ID NO:1 and the polypeptide of SEQ ID NO:2.

In general, DAS181 can be: A) a polypeptide comprising (or consisting of or consisting essentially of) the amino acid sequence of SEQ ID NO:1; B) a polypeptide comprising (or consisting of or consisting essentially of) the amino acid sequecne of SEQ ID NO:2; or C) a mixture of a polypeptides comprising (or consisting of or consisting essentially of) SEQ ID NO:1 and polypeptides comprising (or consisting of or consisting essentially of) SEQ ID NO:2.

For administering DAS181 to the central respiratory tract (asthma, COPD) or to the upper respiratory tract (influenza, parainfluenza), it is desirable to have uniform microparticle formulations with particles of mass median aerodynamic diameter (MMAD) between about 3 microns to about 8 microns and a GSD of between about 1.2 to 2.0. In general, depending somewhat on the flow rate of the inhalation, particles with MMAD between about 3 microns to about 5 microns are expected to deposit in the lower respiratory tract, particles with MMAD between about 5 microns to about 8 microns are expected to deposit in the central to upper respiratory tract, and particles of about 8 microns to about 10 or 11 microns are expected to deposit primarily in the upper respiratory tract.

Microparticles that are smaller than about 2 or 2.5 microns can reach alveoli of the lungs and release the drug, where it can be absorbed into the bloodstream. In some cases it is desirable that particles smaller than about 2.0 or 2.5 microns are present at a very low level or are essentially absent from pharmaceutical formulations not intended for pulmonary delivery or systemic absorption.

Thus, in some embodiments, provided herein are uniform-sized microparticle formulations of DAS181 (polypeptides comprising or consisting of SEQ ID NO:1, polypeptides comprising or consisting of SEQ ID NO:2 or in some instances a combination comprising polypeptides comprising or consisting of SEQ ID NO:1 and polypeptides comprising or consisting of SEQ ID NO:2) or other active agents useful for preventing or treating infections and other disorders of the respiratory tract such as influenza, parainfluenza, asthma and COPD, wherein the microparticles are of a size that is suitable for deposition in the central to lower respiratory tract. For optimal deposition of the microparticles at target sites of the infection or disorder (upper respiratory for influenza, central respiratory for asthma), the majority of the microparticles in the formulation must not be (a) so big that they are trapped at the front end in the mouth (e.g., greater than about 10.5 or 11 microns); or (b) so small that they are deposited deep in the lungs and absorbed systemically into the blood stream through the alveoli (e.g., less than about 2.0 or 2.5 microns).

In many cases, the microparticles themselves are relative homogeneous, i.e., the formulation components, e.g., the API (DAS181) are not segregated and are instead generally evenly distributed throughout the microparticles. Further, the fine particle fraction (FPF) containing microparticles that are smaller than the desired size for deposition to the target site of interest is less than 10%, generally less than about 8%, 7%, 6%, 5%, 4%, 3.5%, 3%, 2.5%, 2%, 1.5% or 1%.

In many cases, the microparticles themselves are essentially homogenous with respect to the API, i.e., the formulation components, e.g., the API is essentially one specific polypeptide of DAS181 of one sequence, e.g., SEQ ID NO: 1 or SEQ ID NO: 2. In such homogenous batches, the API is not segregated and is instead generally evenly distributed throughout the microparticles.

In certain cases, the microparticles themselves are heterogeneous with respect to the API, i.e., the formulation components, e.g., the API is comprised of one or more than one ingredient, i.e., polypeptides of DAS181 of two different sequences, e.g., SEQ ID NO: 1 together in a batch SEQ ID NO: 2. In such heterogeneous batches, the heterogeneous API polypeptides are not segregated and are instead generally evenly distributed throughout the microparticles.

Microparticle Formulation II

In some embodiments, DAS181 (comprising or consisting of SEQ ID NO:1 or comprising or consisting of SEQ ID NO:2 or in some instances, a batch with polypeptides comprising or consisting of SEQ ID NO:1 and polypeptides comprising or consisting of SEQ ID NO:2) is provided in the following microparticle formulation:

Formulation II—not anhydrous (wt/wt %):

a) DAS181: 64.5-64.7% of SEQ ID NO:1 or SEQ ID NO:2 or a batch comprising SEQ ID NO:1 and SEQ ID NO:2
b) Histidine free base: 4.3-4.6%
c) Histidine HCl: 5.8-6.3%
d) Trehalose: 9.0-9.7%
e) Magnesium sulfate: 4.6-5.9%
g) Water: 10.0% (depending on humidity of storage conditions)

The microparticles can also include small amounts of sodium acetate (less than 1%, less than 0.5%, less than 0.1%, less than 0.05%, e.g., 0.03%); small amounts of calcium chloride (less than 1%, less than 0.5%, less than 0.3%, e.g., 0.3%); and small amounts of acetic acid (less than 1%, less than 0.5%, less than 0.1%, less than 0.05%, e.g., 0.02%). Small amounts of residual isopropanol can sometimes be present (less than 1%, less than 0.5%, less than 0.1%, less than 0.05%, less than 0.01%).

Formulation II—anhydrous (wt/wt %):

a) DAS181: 71.7-71.9% of SEQ ID NO:1 or SEQ ID NO:2 or a batch comprising SEQ ID NO:1 SEQ ID NO:2
b) Histidine free base: 4.8-5.1%
c) Histidine HCl: 6.5-7.0%
d) Trehalose: 10.7-10.1%
e) Magnesium sulfate: 5.1-6.5%

The microparticles can also include small amounts of sodium acetate (less than 1%, less than 0.5%, less than 0.1%, less than 0.05%, e.g., 0.03%); small amounts of calcium chloride (less than 1%, less than 0.5%, less than 0.3%, e.g., 0.3%); and small amounts of acetic acid (less than 1%, less than 0.5%, less than 0.1%, less than 0.05%, e.g., 0.02%). Small amounts of residual isopropanol can sometimes be present (less than 1%, less than 0.5%, less than 0.1%, less than 0.05%, less than 0.01%). In some embodiments the formulation is free of citrate.

In one embodiment the method of preparing Formulation II includes the following steps:

(a) An Excipient Solution (pH 6) containing histidine, trehalose, magnesium sulfate and calcium chloride is prepared by combining stock solutions is prepared and sterile filtered.
(b) The Excipient Solution is added, with mixing, to a compounding vessel containing DAS181 protein (SEQ ID NO:1 or SEQ ID NO:2 or a batch comprising SEQ ID NO:1 and SEQ ID NO:2) at 125 mg/ml initial concentration of DAS 181.
(c) Sterile filtered isopropanol is added to the compound vessel with mixing to form the Feedstock Solution. The final composition of the Feedstock Composition is as follows: 70 mg/ml DAS181 (SEQ ID NO:1 or SEQ ID NO:2 or a batch with polypeptides comprising SEQ ID NO:1 and polypeptides comprising SEQ ID NO:2), 25% isopropanol, 4.99 mg/ml histidine, 6.80 mg/ml histidine-HCl, 10.50 mg/ml trehalose, 5.06 mg/ml magnesium sulfate, 0.21 mg calcium chloride, 0.05 mg/ml sodium acetate, 0.02 mg/ml acetic acid. The pH of the solution is 6.0. The time between initiating the addition of isopropanol and starting the lyophilization cycle is between 60 minutes.
(e) Stainless Steel trays that have undergone depyrogenation are each filled with 18 g of the Feedstock Solution, using a metering pump.
(f) The filled Stainless Steel trays are subjected to a Lyophilization Cycle as follows:
   a. the trays are gasketed and placed in the lyophilizer shelves at 25° C. for 5 minutes;
   b. the temperature of the shelves is lowered to −45° C. at a rate of −0.5° C./minute;
   c. primary drying is accomplished by setting the condenser to less than −80° C., applying a vacuum of 125 mTorr and increasing the temperature to −0° C. at a ramp rate of 1° C./minute and then holding for 60 hrs;
   d. the secondary drying is accomplished increasing the temperature to 30° C. at a rate of 1° C./minute and then holding for 6 hrs; and
   e. the vacuum is released and the lyophilizer is back-filled with nitrogen to prevent oxidation of the microparticle formulation before transferring into bottles for bulk mixing and aliquoting the bulk powder for storage at ≤−15° C.

Microparticles of Formulation II can have one or more of: an MMAD of 6.5 microns (or 2-8 microns. 3-8 microns or 5-7), a GSD of 1.5-1.7 (or 1.3-1.9 or 1.4-1.8), a FPF (volume % below 5 microns) of 6.6% (less than 35%, 30%, 25%, 20%, 15%, 10% or 5%) and, a Tg of 38° C.

Thus, in some embodiments, the microparticles have a MMAD of 3-8 (5-7) microns (6.2-6.8 microns) with a GSD of 1.3-1-6 (1.4-1.6), a FPF of less than 9% (less than 8%, less than 7%, about 6-7%) and comprise (on a weight % basis) DAS181 (SEQ ID NO:1 or SEQ ID NO:2 or a batch comprising SEQ ID NO:1 and SEQ ID NO:2): 60-70% (62-68%, 64-66%, 65%); Histidine free base: 3-6% (4-5%); Histidine HCl: −5-9% (5-7%, 8-9%); Trehalose: 7-11% (8-10%, 8.5-9.5%); Magnesium sulfate: 4-8% (5-7%, 4-6%); and Water: 6-12% (8-12%, 9-11%). The microparticles can also include small amounts of sodium acetate (less than 1%, less than 0.5%, less than 0.1%, less than 0.05%, e.g., 0.03%); of calcium chloride (less than 1%, less than 0.5%, less than 0.4%, less than 0.3%, e.g., 0.1-0.3%) and small amounts of acetic acid (less than 1%, less than 0.5%, less than 0.1%, less than 0.05%, e.g., 0.01%). Small amounts of residual isopropanol can sometimes be present (less than 1%, less than 0.5%, less than 0.1%, less than 0.05%, less than 0.01%).

When the microparticles of Formulation II are anhydrous they can comprise (on a weight % basis) DAS181 (SEQ ID NO:1 or SEQ ID NO:2 or a batch comprising SEQ ID NO:1 and SEQ ID NO:2): 69-74% (70-73%, 71-72%, 72%); Histidine free base: 3-8% (4-7%, 4-6%); Histidine HCl: 4-9% (5-8%, 6-7%); Trehalose: 8-12% (9-11%, 8-10%); Magnesium sulfate: 4-8% (5-7%, 6-7%). The microparticles can also include small amounts of sodium acetate (less than 1%, less than 0.5%, less than 0.1%, less than 0.05%, e.g., 0.03%); small amounts of calcium chloride (less than 1%, less than 0.5%, less than 0.1%, less than 0.05%, e.g., 0.03%) and small amounts of acetic acid (less than 1%, less than 0.5%, less than 0.1%, less than 0.05%, e.g., 0.01%). Small amounts of residual isopropanol can sometimes be present (less than 1%, less than 0.5%, less than 0.1%, less than 0.05%, less than 0.01%).

Microparticle Formulation I

In some embodiments, DAS181 (comprising or consisting of SEQ ID NO:1 or comprising or consisting of SEQ ID NO:2 or in some instances, a batch with polypeptides comprising or consisting of SEQ ID NO:1 and polypeptides comprising or consisting of SEQ ID NO:2) is provided in the following microparticle formulation:

Formulation I—not anhydrous (wt/wt %):

a) DAS181: 86.7% of SEQ ID NO:1 or SEQ ID NO:2 or a batch comprising SEQ ID NO:1 and SEQ ID NO:2)
b) sodium sulfate 2.5%
c) Water:10.0% (depending on humidity of storage conditions)

The microparticles can also include small amounts of sodium acetate (less than 1%, less than 0.5%, less than 0.1%, less than 0.05%, e.g., 0.03%); small amounts of calcium chloride (less than 1%, less than 0.5%, less than 0.1%, less than 0.05%, e.g., 0.03%) and small amounts of acetic acid (less than 1%, less than 0.5%, less than 0.1%, less than 0.05%, e.g., 0.01%). Small amounts of residual isopropanol can sometimes be present (less than 1%, less than 0.5%, less than 0.1%, less than 0.05%, less than 0.01%).

Formulation I—anhydrous (wt/wt %):

a) DAS181: 96.3% SEQ ID NO:1 or SEQ ID NO:2 or a batch comprising SEQ ID NO:1 and SEQ ID NO:2)
b) sodium sulfate 2.7%

The microparticles of Formulation I can also include small amounts of sodium acetate (less than 1%, less than 0.8%, less than 0.7%, less than 0.6%); small amounts of calcium chloride (less than 1%, less than 0.5%, less than 0.4%) and small amounts of acetic acid (less than 1%, less than 0.5%, less than 0.4%, less than 0.3%, e.g., 0.2%). Small amounts of residual isopropanol can sometimes be present (less than 1%, less than 0.5%, less than 0.1%, less than 0.05%, less than 0.01%).

Microparticles of Formulation I can have one or more of: an MMAD of 4-7 microns (or 2-8 microns. 3-8 microns or 5-7 microns), a GSD of 1.5-1.7 (or 1.3-1.9 or 1.4-1.8), a FPF (volume % below 5 microns) of 8% (less than 35%, 30%, 25%, 20%, 15%, 10% or 5%) and, a Tg of 38° C.

Thus, in some embodiments, the microparticles have a MMAD of 3-8 (5-7) microns (6.2-6.8 microns) with a GSD of 1.3-1-6 (1.4-1.6), a FPF of less than 9% (less than 8%, less than 7%, about 6-7%) and comprise (on a weight % basis) DAS181 (SEQ ID NO:1 or SEQ ID NO:2 or a batch comprising SEQ ID NO:1 and SEQ ID NO:2):

Microparticle Formulations

The microparticle formulations obtained by the methods provided herein are of a relatively uniform size distribution, i.e., relatively monodisperse, with a geometric standard deviation (GSD) of between about 1.2 and 2.0, generally between about 1.2 and 1.5, 1.6, 1.7 or 1.8. The particles are also homogeneous, i.e., the formulation components are not segregated and are evenly distributed throughout the particles. Further, the fine particle fraction (FPF) containing microparticles that are smaller than 5 microns is less than 10%, generally less than about 8%, 7%, 6%, 5%, 4%, 3.5%, 3%, 2.5%, 2%, 1.5% or 1%.

In some embodiments, in addition to DAS 181 SEQ ID NO:1 or SEQ ID NO:2 or a batch comprising SEQ ID NO:1 and SEQ ID NO:2), microparticles can include an additional active agent which can be a macromolecule such as a protein, a nucleic acid, a carbohydrate, a lipid, a fatty acid, a polysaccharide or a carbohydrate- or polysaccharide-protein conjugate. In other embodiments, the active agent or API can be a small molecule such as a prostaglandin, an antibiotic selected from among aminoglycosides, ansamycins, carbacephem, carbapenems, cephalosporins, macrolides, penicillins, quinolones, sulfonamides and tetracyclines, an antiviral agent such as zanamivir or oseltamivir phosphate, or a chemotherapeutic agent selected from among alkylating agents, anthracyclines, cytoskeletal disruptors, epothilones, inhibitors of topoisomerase II, nucleotide analogs, platinum-based agents, retinoids and vinca alkaloids.

In the methods provided herein, the microparticle formulation of the protein can also be tailored to a desired predetermined particle size and uniform size distribution by modifying one or more additional parameters or steps, including one or more of the following: (1) the concentration of the protein in the feedstock solution; (2) the nature and/or concentration of the counterion in the feedstock solution; (3) the nature and/or concentration of the organic solvent in the feedstock solution; (4) the concentration of excipient; (5) the volume of feedstock solution in the lyophilization trays; and (6) one or more controlled temperature ramping (temperature decreasing and/or temperature increasing) steps for forming and isolating the resulting microparticles.

Also provided herein are methods of making stable microparticle formulations and the resulting stable microparticle formulations in which the active agent (or API, for a pharmaceutical formulation) is protected from degradation or aggregation resulting from materials present in the packaging container or delivery system. The methods provided herein include the steps of: mixing together: (i) a solution of an active agent in an aqueous solvent, (ii) a counterion selected from among citric acid/citrate, magnesium sulfate, potassium sulfate or calcium sulfate, phosphate, pivalate, rubidium, bromine, perchlorate, itaconate, and any salt, acid, or base form thereof, (iii) one or more scavenging agents and (iv) an organic solvent (e.g., isopropanol); and cooling the resulting mixture (also referred to herein as cocktail solution or feedstock solution) to a predetermined temperature below about 25° C. either gradually or at a cooling rate that can be maintained at a constant fixed value until the mixture is at the predetermined temperature below about 25° C., whereby a composition containing microparticles that include DAS181 SEQ ID NO:1 or SEQ ID NO:2 or a batch comprising SEQ ID NO:1 and SEQ ID NO:2) at about 50% to about 85% wt/wt, the counterion at about 2% to about 6% wt/wt and the scavenging agents at about 8% to about 40% wt/wt is formed. The resulting microparticles can be separated from the mixture to remove components other than the microparticles by, for example, sedimentation, filtration and/or freeze-drying.

The resulting dry microparticles, in certain embodiments, can have a composition of between about 50% to about 75% wt/wt of SEQ ID NO:1 or SEQ ID NO:2 or a batch comprising SEQ ID NO:1 and SEQ ID NO:2), between about 2% to about 6% wt/wt of the counterion, between about 5% to about 40% wt/wt of each scavenging agent and between about 5% to about 10% residual moisture. The scavenging agent can be a primary or secondary amine, a chelator, an antioxidant, a sugar, or combinations thereof and generally is present in at least a 100-fold excess, up to about a 150, 200, 250, 300, 350, 400, 450, 500, 550, 600, 650, 700, 750, 800, 850, 900, 950 or a 1000 fold or more molar excess relative to the aldehyde(s) present in the material used to package the microparticles. The scavenging agent is incorporated into the microparticles obtained by the methods provided herein, and can protect the active agent against the damaging effects of some materials, such as aldehydes, that may be present in a packaging container or delivery system such as HPMC capsules, certain gel capsules, pullulan polysaccharide capsules and aluminum foil laminate blister packs.

In some embodiments of the method, the active agent is a protein and in particular embodiments, the protein is DAS181 SEQ ID NO:1 or SEQ ID NO:2 or a batch comprising SEQ ID NO:1 and SEQ ID NO:2). In other embodiments, the scavenging agent is histidine. In yet other embodiments, the scavenging agent is tryptophan. In further embodiments, combinations of scavenging agents, such as an amino acid and a sugar, more than one amino acid, or more than one amino acid and a sugar, are used; in particular embodiments, the combinations of scavenging agents are histidine and trehalose, histidine and sucrose, glycine and sucrose, histidine, glycine and sucrose, or histidine and tryptophan. In some embodiments, the microparticle formulations containing an active agent, a counterion and a scavenging agent as provided herein can further be tailored to a desired predetermined particle size and uniform size distribution by applying a constant, fixed cooling rate to the feedstock solution for cooling the feedstock solution from a temperature above or at 25° C. to a predetermined temperature below 25° C., whereby microparticles are formed. Additional parameters or steps that can be used to obtain a desired particle size and/or size distribution can include one or more of the following: (1) the concentration of the active agent in the feedstock solution; (2) the nature and/or concentration of the counterion in the feedstock solution; (3) the nature and/or concentration of the organic solvent in the feedstock solution; (4) the concentration of excipient; (5) the volume of feedstock solution in the lyophilization trays; and (6) one or more controlled temperature ramping (temperature decreasing and/or temperature increasing) steps for forming and isolating the resulting microparticles.

Also provided herein are microparticles of a protein containing between about 50% to about 85% wt/wt of the protein, about 2% to about 6% wt/wt of a counterion selected from among citric acid/citrate, magnesium sulfate, potassium sulfate or calcium sulfate, phosphate, pivalate, rubidium, bromine, perchlorate, itaconate, and any salt, acid, or base form thereof, and about 8% to about 40% wt/wt of one or more scavengers. In some embodiments, the protein is DAS181 (SEQ ID NO:1 or SEQ ID NO:2 or a batch with polypeptides comprising SEQ ID NO:1 and polypeptides comprising SEQ ID NO:2) and in further embodiments, the scavenging agent is present in about 9% to about 11% wt/wt of the dry powder microparticles. In some embodiments, the scavenging agent(s) present in the DAS181 microparticle formulations is histidine, histidine/histidine HCl, histidine/trehalose, histidine/tryptophan, histidine/sucrose, glycine/sucrose, or histidine/glycine/sucrose.

Exemplary feedstock solutions used to prepare microparticle formulations of DAS181 according to the methods provided herein can include between about 10 mg/ml to about 70 mg/ml DAS181 (SEQ ID NO:1 or SEQ ID NO:2 or a batch with polypeptides comprising SEQ ID NO:1 and polypeptides comprising SEQ ID NO:2) and one or more of the following: histidine from about 0.1-about 11 mg/ml, glycine from about 0.006-about 7 mg/ml, trehalose or sucrose from about 1.93-about 11 mg/ml, tryptophan from about 1.11-about 3.5 mg/ml, magnesium sulfate from about 0.24-about 6.8 mg/ml, calcium chloride from about 0.03-about 0.21 mg/ml.

Also provided herein are uniform, stable microparticle formulations of DAS181 that include a counterion at 2% to about 6% wt/wt, a scavenging agent that is an amine at about 9% to about 20% wt/wt, and a sugar. Also provided herein are microparticle formulations containing an active agent, a counterion selected from among citric acid/citrate, magnesium sulfate, potassium sulfate or calcium sulfate, phosphate, pivalate, rubidium, bromine, perchlorate, itaconate, and any salt, acid, or base form thereof and a scavenging agent that is a chelator or an antioxidant. In some embodiments, the scavenging agent is ascorbic acid or ascorbic acid phosphate; in other embodiments, the scavenging agent is TETA. In further embodiments, the active agent is a protein.

The methods provided herein for making microparticle formulations can include additional steps. For example, after cooling the feedstock solution at a constant, fixed rate to a predetermined temperature below about 25° C. for forming the microparticles, the cooled solution can be held at that predetermined temperature for a specified period of time to remove unincorporated components of the microparticles by freeze-drying. The microparticles can further be heated in primary and optionally secondary drying steps to remove volatile components by sublimation. In some embodiments, the resulting microparticles are further packaged into materials containing formaldehyde and/or other aldehydes, such as hydroxypropyl methylcellulose (HPMC), aluminum foil laminates, gel capsules or pullulan polysaccharide.

Also provided herein are microparticle formulations that are packaged in materials containing formaldehyde and/or other aldehydes. Such materials include, but are not limited to, hydroxypropyl methylcellulose (HPMC) capsules, certain gel capsules, aluminum foil laminate blister packs and pullulan polysaccharide capsules.

Also provided herein are articles of manufacture that contain a microparticle formulation that includes a sialidase or a sialidase fusion protein in an amount of about 60% to about 75% wt/wt, a counterion and a scavenging agent that is a primary amine in the amount of about 8% to about 11% wt/wt, a packaging material for the formulation, where the material contains formaldehyde and/or other aldehydes, and a label that indicates that the composition is for a therapeutic indication. In one embodiment, the therapeutic indication is influenza. In other embodiments, the therapeutic indication is asthma or COPD. In yet other embodiments, the therapeutic indication is selected from among parainfluenza, RSV, sinusitis, otitis, laryngitis, bronchitis, pneumonia, bronchiectasis, vasculitis, mucous plugging, Wegener's granulomatosis and cystic fibrosis (CF). In some embodiments, the scavenging agent is histidine; in other embodiments, the scavenging agent is a combination of histidine and trehalose. In yet other embodiments, the counterion is selected from among citric acid/citrate, magnesium sulfate, potassium sulfate or calcium sulfate, phosphate, pivalate, rubidium, bromine, perchlorate, itaconate, and any salt, acid, or base form thereof. The packaging material can be a HPMC capsule; in further embodiments, the HPMC capsule is clear. In other embodiments, the packaging material can be a gel capsule, or a pullulan polysaccharide capsule. In yet other embodiments, the article of manufacture further contains a secondary packaging material; in some embodiments, the secondary packaging material is a foil laminate; in particular embodiments, the foil laminate is a cold form foil aluminum laminate blister pack. In some embodiments, the scavenging agent is an amine; in further embodiments, the amine is selected from among lysine, histidine, glycine, arginine, glutamine, glutamic acid, cysteine, alanine, tyrosine, tryptophan, aminoguanidine, cysteamine, serine, carnosine, hydralazine and poly(1-lysine). In one embodiment, the sialidase fusion protein is DAS181 having the sequence set forth in SEQ ID NO:1 or SEQ ID NO:2 or, in some instances, DAS181 is present as a batch with polypeptides comprising SEQ ID NO:1 and polypeptides comprising SEQ ID NO:2; in a particular embodiment, the sialidase fusion protein is DAS181 having the sequence set forth in SEQ ID NO:1 or SEQ ID NO:2 or, in some instances, DAS181 is present as a batch with polypeptides comprising SEQ ID NO:1 and polypeptides comprising SEQ ID NO:2 and the scavenging agent is histidine or a combination of histidine and trehalose.

The articles of manufacture provided herein also can contain an inhaler for pulmonary administration of the composition. In certain embodiments, the inhaler is a dry powder inhaler, a metered dose inhaler or an electrostatic delivery device.

DETAILED DESCRIPTION

A. Definitions

The term "microparticle" as used herein is interchangeable with "microsphere" and refers to particles in the size range (average length, width or diameter) of about or at 0.001 micron (μm) to about or at 500 microns that contain a macromolecule or small molecule that is an active agent of interest, such as a drug or nutritional supplement. Among the microparticles provided herein are those of a size between about 3 microns to about 8 microns mass median aerodynamic diameter (MMAD) and containing active agents, including proteins and, in some embodiments, the sialidase fusion protein DAS181 (SEQ ID NO:1 or SEQ ID NO:2 or a batch with polypeptides comprising SEQ ID NO:1 and polypeptides comprising SEQ ID NO:2), which are for treating respiratory tract diseases of the upper and/or central respiratory tract. The active agent can be a small molecule or a macromolecule. The macromolecule, for example, a protein, nucleic acid, lipid or polysaccharide, or the macromolecule forming the microparticle can be the active agent or can be a carrier for the active agent, such as a drug or a nutritional supplement. The microparticles also can contain synthetic macromolecules including polymers, such as polyethylene glycol (PEG), polylactic acid (PLA), polylactic-co-glycolic acid (PLGA), and natural polymers such as albumin, gelatin, chitosan and dextran.

The term "microparticle" as used herein also generally refers to a particle that is not a solid form of the entire solution from which it is produced; rather, the microparticle as used herein generally is an assembly of a fraction of the components of a solution, including active agents, salts, counterions, solvents, scavenging agents and other ingredients and is formed by a process including, but not limited to, precipitation, sedimentation, phase separation and colloid formation.

The term "dry" or "dry powder" formulation in reference to microparticles, as used herein refers to microparticle formulations that are separated from unincorporated components of the feedstock solution by a process including, but not limited to, precipitation, freeze-drying, sedimentation, phase separation, colloid formation and drying to sublime volatiles in the feedstock solution. The dry powder formulations of microparticles provided herein can include residual moisture, generally at about 15, 14, 13, 12, 11, 10, 9, 8, 7, 6, 5% or less The term "mixture" is used interchangeably with "cocktail solution" or "feedstock solution" herein and refers to the homogeneous mixture distribution of ingredients obtained just prior to lyophilization to form the microparticle formulation; the distinct ingredients of the feedstock solution are recognizable only at the molecular level.

As used herein, "shelf life" or "stability" refers to the time after preparation of the microparticle composition that the composition retains at least about or 70%, 80%, 85%, 90%, 91%, 92%, 93%, 94%, 95%, 96%, 97%, 98% or 99% of the initial activity that is present in the composition and other general characteristics of the microparticles such as no more than about 1-2% aggregate formation (e.g., dimers and higher order oligomer formation) over time and the retention of size, shape, color and aerodynamic particle size distribution. Thus, for example, a composition that is stable for or has a shelf life of 30 days at room temperature, defined herein as range of between about 18° C. to about 25° C., 26° C., 27° C. or 28° C., would have at least about 70%, 80%, 85%, 90% 91%, 92%, 93%, 94%, 95%, 96%, 97%, 98% or 99% of the initial amount of the activity of protein present in the composition at 30 days following storage at 18° C. to about 25° C., 26° C., 27° C. or 28° C. The shelf life of the microparticle compositions provided herein generally is at least about 10 days at 55° C., at least about 2-3 weeks at 42° C., at least about 6-8 weeks at 37° C., and at least about eight months or greater at 25° C.; however, microparticles compositions of any length of shelf life at any temperature that are produced by the methods provided herein are contemplated herein.

As used herein, "organic solvent" refers to a solvent that is an organic compound, which is any member of a large class of chemical compounds whose molecules contain carbon and hydrogen. Such solvents can include, for example, compounds from the following classes: aliphatic or aromatic alcohols, polyols, aldehydes, alkanes, alkenes, alkynes, amides, amines, aromatics, azo compounds, carboxylic acids, esters, dioxanes, ethers, haloalkanes, imines, imides, ketones, nitriles, phenols and thiols. In some embodiments of the methods provided herein, the organic solvents used are not polymers. In other embodiments, the organic solvent used is a solvent other than ethanol.

As used herein, an "aqueous solvent" refers to water, or a mixture of solvents that contains at least about 50% or 50%, at least about 60% or 60%, at least about 70% or 70%, or about or at 75%, 80%, 85%, 90%, 95%, 96%, 97%, 98%, 99% or higher amounts of water. The term "aqueous solvent" as used herein also refers to solutions containing water as a solvent, such as buffers, salt solutions, solutions containing counterions, and other solutes that are soluble in water.

As used herein, the term "counterion" refers to a charged or charge-polarizable molecule that can initiate formation of a microparticle from a macromolecule, such as a protein, nucleic acid, lipid or oligosaccharide. For example, in the case of the DAS181 fusion (e.g., SEQ ID NO:1 or SEQ ID NO:2 or a batch comprising SEQ ID NO:1 and SEQ ID NO:2), sodium sulfate, magnesium sulfate and citric acid are suitable counterions because they can initiate the formation of microparticles in the methods provided herein. The suitability of a charged molecule as a counterion can be determined empirically based on parameters including, but not limited to, the type of protein, the pH, the ionic strength, the type of organic solvent used, and the presence of salts and additional ingredients including the active agent(s). As provided and described herein, counterions can be anionic or having a net negative charge or charge-polarizable group(s), cationic or having a net positive charge or charge-polarizable group(s), or zwitterionic and possessing both negative and positive charged or charge-polarizable groups.

As used herein, the term "cooling" at a "constant, fixed (or preset) rate" means that the cooling rate is set at a predetermined value (i.e., fixed, or preset) and this rate is then applied, within a reasonable variation of about +/−10-15% of the preset value, throughout the cooling process (i.e., constant). Thus, when the feedstock solution from which the microparticles are formed is cooled from a temperature above or at about 25° C. to a predetermined temperature below about 25° C. to form the microparticles, the cooling rate is maintained at the same value regardless of the changing temperature differential during cooling, i.e., regardless of the difference between the temperature of the cocktail solution at any given time during the cooling process and the final predetermined temperature to which it is cooled. The fixed, constant cooling rate at which the feedstock solution is cooled to a predetermined temperature below about 25° C. can be preset by a computer program (e.g., programming the lyophilizer to cool the feedstock solution at a preset, fixed rate) or by mechanical means, e.g., stirring the feedstock solution in a manner that maintains a constant cooling rate. The value of the fixed cooling rate can be selected depending on the desired size of the microparticles and generally can be between about 0.1° C./min to about 1° C./min. For example, for microparticle formation of a protein, such as DAS181 (SEQ ID NO:1 or SEQ ID NO:2 or a batch with polypeptides comprising SEQ ID NO:1 and polypeptides comprising SEQ ID NO:2), where the microparticles are formed by cooling the sample from a temperature of about 25° C. to a temperature of between about −45° C. to −55° C., the rate of cooling can be in the range of about between about 0.1, 0.2, 0.3, 0.4, 0.5, 0.6, 0.7, 0.8, 0.9 or 1.0° C./min. In some embodiments, when the active agent is DAS181, the cooling rate is preset to a value of about 0.4° C./min or 0.5° C./min The terms "ramping," "controlled temperature ramping," "controlled cooling," "controlled rate of cooling" "controlled heating" or "controlled rate of heating" as used herein refer to heating or cooling steps that are performed at a specified rate. "Holding" as used herein refers to a sample or reaction or composition being maintained at a steady temperature, within a range above or below the steady temperature of 0.1, 0.2, 0.3, 0.4, 0.5, 0.6, 0.7, 0.8, 0.9, 1.0, 1.2, 1.4, 1.5, 1.7, 2.0 or more up to about 2.5 or 3° C.

The term "gradual cooling" or "gradually cooling" or "gradually cooled" as used herein means that the rate at which the temperature of the feedstock solution is lowered to a predetermined temperature at which microparticles are formed can be subject to or determined by the temperature differential at any given time between that of the feedstock solution and the predetermined temperature to which it is being cooled. Thus, the rate of cooling can be variable and fluctuate during gradual cooling, as it is dependent on a temperature differential that can change as cooling progresses, can generally vary between about 0.5° C. per minute and 15° C. per minute and typically is at least about 1° C. per minute.

The term "geometric standard deviation" or "GSD" as used herein is a term of art that is a measure of uniformity of the size of the microparticles in a formulation. A GSD of "1" means that all microparticles of the formulation have the same size, while a GSD of "5" generally indicates an un-uniform or polydisperse formulation. As used herein, a "monodisperse" or "uniform" microparticle formulation means that the GSD of the formulation is between about 1.0-2.0, generally about 1.1, 1.2, 1.3, 1.4, 1.5, 1.6, 1.7 or 1.8

The term "fine particle fraction" or "FPF," as used herein, is a term of art that is a measure of the fraction of particles of a microparticle formulation that are below a size considered suitable for deposition at the site of interest. For example, in the case of microparticles to be delivered to the central or upper respiratory tract, microparticles that are greater than about 2 microns, preferably between about 3 microns to about 10 microns are considered suitable for administration. This means that the FPF of the formulation below about 3.5, 3.4, 3.3, 3.2, 3.1, 3.0, 2.9, 2.8, 2.7, 2.6, 2.5, 2.4, 2.3, 2.0 or fewer microns generally should be low, of the order of 5%, 4%, 3%, 2%, 1%, 0.5% or less.

The term "particle size distribution" or "PSD" as used herein is a term of art that generally is an absolute measure of particle size and can be measured, for example, by laser diffraction (e.g., Sympatec HELOS Laser Diffraction System) or other methods known to those of skill in the art. In a laser diffraction-based method, the sizes of the particles of the microparticle formulation are determined based on the differences in the patterns of laser light diffraction generated by different sized particles. The diffracted light of a particular distribution of intensity is collected by a multi-level photodetector and is converted mathematically to extract information about the particle size.

The term "scavenger" or "scavenging agent" as used herein refers to a compound or composition that is a component of the microparticle formulations provided herein and protects the microparticle formulations provided herein from damage, degradation, aggregation, oligomerization or any transformation that destabilizes the formulation or the active agent in the formulation and/or decreases its activity over time. In some embodiments, the destabilizing substances are present in the materials used to package the microparticle formulations or are a byproduct arising during preparation of the materials used to packae the formulations, such as aldehydes in hydroxypropyl methylcellulose (HPMC) capsules, pullulan polysaccharide capsules or laminate foil blister packs. In some embodiments, the scavenging agent can exert its protective effect by reacting with the destabilizing substance at a rate that is faster than the rate of reaction between the active agent and the destabilizing substance. In other embodiments, the scavenging agent can protect the active agent from damage by forming a complex with groups on the active agent that would otherwise react with the destabilizing substances to form degradation products, aggregates, oligomers or other such products. Among the scavenging agents used in the preparation of microparticle formulations are amines, generally primary or secondary amines, chelators, antioxidants, sugars or combinations thereof.

B. Methods for Preparing Microparticle Formulations of Uniform Size

Provided herein are methods of producing uniform sized microparticle formulations of a macromolecule or small molecule active agent, wherein the resulting microparticles are of a desired predetermined size and have a narrow range of size distribution (geometric standard deviation, i.e., GSD of between 1.2-1.6). The methods provided herein include the steps of mixing together a solution of an active agent in an aqueous solvent, a counterion and an organic solvent and cooling the resulting mixture (also referred to herein as cocktail solution or feedstock solution) to a predetermined temperature below about 25° C., generally between about −45° C. to about −60° C., at a cooling rate that is maintained at a constant, preset and fixed value until the mixture is at the predetermined temperature below about 25° C., whereby a composition containing uniform sized microparticles of the active agent is formed. The resulting microparticles can be separated from unincorporated components in the feedstock solution by, for example, sedimentation, filtration and/or freeze-drying. The methods can further include steps of holding the feedstock solution at the predetermined temperature (generally between about −45° C. to about −60° C.) at which the microparticles are formed, then ramping up the temperature for primary and optionally secondary drying steps, whereby volatiles present in the microparticle formulations can be removed by sublimation. Several components and steps used in the methods provided herein, e.g., the types of active agents, counterions and organic solvents, cooling to form the microparticles, freeze-drying the resulting microparticles, have been described in detail elsewhere and are incorporated by reference herein (see, e.g., published U.S. Applications Serial Nos. 20070190163 A1 and its continuation, 20100166874 A1, both of which are titled "Technology for Preparation of Macromolecular Microparticles" and published U.S. Application Serial No. 20090098207 A1 titled "Technology for the Preparation of Microparticles").

In the methods provided herein, microparticle formulations of a desired size can be obtained by choosing a cooling rate that can produce particles of that size. The cooling rate can be determined empirically for a given mixture of an active agent, counterion and organic solvent, using screening methods as described elsewhere (see, e.g., published U.S. Applications Serial Nos. 20070190163 A1 and its continuation, 20100166874 A1, both of which are titled "Technology for Preparation of Macromolecular Microparticles" and published U.S. Application Serial No. 20090098207 A1 titled "Technology for the Preparation of Microparticles"). In general, a faster cooling rate produces smaller particle sizes, while a slower cooling rate produces larger particle sizes. To obtain uniform formulations, the cooling rate can further be maintained at a constant, fixed value as the feedstock solution is cooled from a temperature at or above 25° C. to a predetermined temperature below about 25 C (generally between about −45° C. to about −60° C.) whereby microparticles are formed.

The methods provided herein further produce microparticle formulations that are uniform or monodisperse, with a GSD of between 1.0-1.8, generally between about 1.2-1.6. The uniformity of the size is achieved by maintaining the cooling rate of the feedstock solution at a constant, fixed value, beginning at a temperature above or at about 25° C. until the mixture is cooled to the desired predetermined temperature below about 25° C. and microparticles are formed. The cooling rate can be maintained at a fixed value by mechanical means, such as stirring the feedstock solution to cool the solution at a specified preset rate, or by programming a computer to maintain a fixed cooling rate, regardless of the difference in temperature between the feedstock solution at any given time during the cooling process and the final predetermined temperature to which it is cooled for microparticle formation.

For example, in the case of the sialidase fusion protein DAS181, whose sequence is set forth in SEQ ID NO:1 and SEQ ID:2, when the methods employ faster cooling rates and counterions such as sodium sulfate and magnesium sulfate, smaller microparticles (value between about 3 microns to about 8 microns mass median aerodynamic diameter (MMAD)) of DAS181 (SEQ ID NO:1 or SEQ ID NO:2 or a batch with polypeptides comprising SEQ ID NO:1 and polypeptides comprising SEQ ID NO:2) are formed. When the methods employ slower cooling rates and counterions such as citrate, larger microparticles (value between about 8 microns to about 11 microns MMAD) of DAS181 (SEQ ID NO:1 or SEQ ID NO:2 or a batch with polypeptides comprising SEQ ID NO:1 and polypeptides comprising SEQ ID NO:2) are formed.

In particular embodiments, provided herein are methods of making uniform microparticle formulations of DAS181 (SEQ ID NO:1 or SEQ ID NO:2 or a batch with polypeptides comprising SEQ ID NO:1 and polypeptides comprising SEQ ID NO:2) with a mass median aerodynamic diameter (MMAD) that has a value between about 3 microns to about 8 microns (e.g., 5-7 microns or 6-7 microns) and a geometric standard deviation (GSD) of between about 1.2 to about 2.0.

In some cases, e.g., acute parainfluenza in an immunocompromised patient, it is useful to treat with microparticles having a MMAD of about 3-8 microns (5.5-7.5 microns), which permits their deposition at in the lower portion of the respiratory tract, while avoiding deposition in the deep lung, e.g., alveoli and/or absorption into the blood stream, which could compromise their pharmacokinetic and/or safety profiles.

In the methods provided herein, the microparticle formulation of the protein can also be tailored to a desired predetermined particle size and uniform size distribution by modifying one or more additional parameters or steps, including one or more of the following: (1) the concentration of the protein in the feedstock solution; (2) the nature and/or concentration of the counterion in the feedstock solution; (3) the nature and/or concentration of the organic solvent in the feedstock solution; (4) the concentration of excipient; (5) the volume of feedstock solution in the lyophilization trays; and (6) one or more controlled temperature ramping (temperature decreasing and/or temperature increasing) steps for forming and isolating the resulting microparticles.

The methods provided herein for making microparticle formulations can include additional steps. For example, after cooling the feedstock solution at a constant, fixed rate to a predetermined temperature below about 25° C. for forming the microparticles, the cooled solution can be held at that predetermined temperature for a specified period of time to remove unincorporated components of the microparticles by freeze-drying. The microparticles can further be heated in primary and optionally secondary drying steps to remove volatile components by sublimation. In some embodiments, the resulting microparticles are further packaged into materials containing formaldehyde and/or other aldehydes, such as hydroxypropyl methylcellulose (HPMC), aluminum foil laminates, gel capsules or pullulan polysaccharide.

C. Uniform Microparticle Formulations

Also provided are uniform microparticle formulations prepared according to the methods provided herein. In some embodiments, the active agent or API in the formulation is for treating diseases that affect the respiratory tract such as influenza, asthma and COPD. An example of an API that can be used to treat respiratory diseases and disorders is the sialidase fusion protein, DAS181 (SEQ ID NO:1 or SEQ ID NO:2 or a batch with polypeptides comprising SEQ ID NO:1 and polypeptides comprising SEQ ID NO:2). For administering DAS181 to the central and lower respiratory tract it is desirable to have uniform microparticle formulations with particles of mass median aerodynamic diameter (MMAD) between about 3 microns to about 8 microns and a GSD of between about 1.2 to 2.0. In general, particles with MMAD between about 3 microns to about 5 microns are expected to deposit in the lower respiratory tract, particles with MMAD between about 5 microns to about 8 microns are expected to deposit in the central to upper respiratory tract, and particles of about 8 microns to about 10 or 11 microns are expected to deposit primarily in the upper respiratory tract. Microparticles that are smaller than about 2 or 2.5 microns, upon inhalation, can reach alveoli of the lungs and release the drug, where it can be absorbed into the bloodstream and could compromise the therapeutic (pharmacokinetic) profile or safety profile of the drug. For such drugs, including DAS181, it is desirable that particles smaller than about 2.0 or 2.5 microns are present at a very low level or are essentially absent from pharmaceutical formulations not intended for pulmonary delivery or systemic absorption.

Thus, in some embodiments, provided herein are uniform-sized microparticle formulations of DAS181 (SEQ ID NO:1 or SEQ ID NO:2 or a batch with polypeptides comprising SEQ ID NO:1 and polypeptides comprising SEQ ID NO:2) or other active agents useful for preventing or treating infections and other disorders of the respiratory tract such as influenza, parainfluenza, asthma and COPD, wherein the microparticles are of a size that is suitable for deposition in the throat, trachea or bronchi. For optimal deposition of the microparticles at target sites of the infection or disorder (upper respiratory for influenza, central respiratory for asthma), the microparticles must not be (a) so big that they are trapped at the front end in the mouth (e.g., greater than about 10.5 or 11 microns); or (b) so small that they are deposited deep in the lungs and absorbed systemically into the blood stream through the alveoli where they are not active and/or can be toxic (e.g., less than about 2.0 or 2.5 microns).

The microparticle formulations obtained by the methods provided herein are of a uniform size distribution, i.e., monodisperse, with a geometric standard deviation (GSD) of between about 1.2 and 2.0. Because of their uniform or monodisperse character, the DAS181 (SEQ ID NO:1 or SEQ ID NO:2 or a batch with polypeptides comprising SEQ ID NO:1 and polypeptides comprising SEQ ID NO:2) microparticle formulations provided herein, which generally are of a size between about 3 microns and about 8 microns, have few to no particles less than about 2.5 microns, thus minimizing undesirable deposition of the drug into the deep lung and/or absorption into the bloodstream. The microparticle formulations are also homogeneous, i.e., the formulation components are not segregated and are evenly distributed throughout the particles. The microparticle formulation may be homogenous, i.e., in the case of DAS181, the API can be comprised of SEQ ID NO:1 or SEQ ID NO:2, or heterogeneous, i.e., in the case of DAS181, the API can be comprised of a batch with polypeptides comprising SEQ ID NO:1 and polypeptides comprising SEQ ID NO:2, with regard to the components of the API. Further, the fine particle fraction (FPF) containing microparticles that are smaller than 5 microns is less than 10%, generally less than about 8%, 7%, 6%, 5%, 4%, 3.5%, 3%, 2.5%, 2%, 1.5% or 1%. In one embodiment, a microparticle formulation of DAS181 (SEQ ID NO:1 or SEQ ID NO:2 or a batch with polypeptides comprising SEQ ID NO:1 and polypeptides comprising SEQ ID NO:2) for the prophylaxis or treatment of influenza has a mass median aerodynamic diameter (MMAD) of 5-8 (6-7) microns, a GSD of 1.4-1.6, an FPF of less than 5% (2-4%) for particle sizes less than 5 microns.

D. Methods of Making Microparticle Formulations that are Stable in their Packaging Also provided herein are methods of making stable microparticle formulations and the resulting stable microparticle formulations in which the active agent (or API, for a pharmaceutical formulation) is protected from degradation or aggregation resulting from materials present in the packaging container or delivery system. The methods provided herein include the steps of:

mixing together: (i) a solution of an active agent in an aqueous solvent, (ii) a counterion selected from among citric acid/citrate, magnesium sulfate, potassium sulfate or calcium sulfate, phosphate, pivalate, rubidium, bromine, perchlorate, itaconate, and any salt, acid, or base form thereof, (iii) one or more scavenging agents and (iv) an organic solvent; and cooling the resulting mixture (also referred to herein as cocktail solution or feedstock solution) to a predetermined temperature below about 25° C. either gradually or at a cooling rate that can be maintained at a constant fixed value until the mixture is at the predetermined temperature below about 25° C., whereby a composition containing microparticles that include the active agent at about 50% to about 85% wt/wt, the counterion at about 2% to about 6% wt/wt and the scavenging agents at about 8% to about 40% wt/wt is formed. The resulting microparticles can be separated from the mixture to remove components other than the microparticles by, for example, sedimentation, filtration and/or freeze-drying.

The resulting dry microparticles, in certain embodiments, can have a composition of between about 50% to about 75% wt/wt of the active agent, between about 2% to about 6% wt/wt of the counterion, between about 5% to about 40% wt/wt of each scavenging agent and between about 5% to about 10% residual moisture. The scavenging agent can be a primary or secondary amine, a chelator, an antioxidant, a sugar, or combinations thereof and generally is present in at least a 100-fold excess, up to about a 150, 200, 250, 300, 350, 400, 450, 500, 550, 600, 650, 700, 750, 800, 850, 900, 950 or a 1000 fold or more molar excess relative to the aldehyde(s) present in the material used to package the microparticles. The scavenging agent is incorporated into the microparticles obtained by the methods provided herein, and can protect the active agent against the damaging effects of some materials, such as aldehydes, that may be present in a packaging container or delivery system such as HPMC capsules, certain gel capsules, pullulan polysaccharide capsules and aluminum foil laminate blister packs.

In some embodiments of the method, the active agent is a protein and in particular embodiments, the protein is DAS181 (SEQ ID NO:1 or SEQ ID NO:2 or a batch with polypeptides comprising SEQ ID NO:1 and polypeptides comprising SEQ ID NO:2). In other embodiments, the scavenging agent is histidine. In yet other embodiments, the scavenging agent is tryptophan. In further embodiments, combinations of scavenging agents, such as an amino acid and a sugar, more than one amino acid, or more than one amino acid and a sugar, are used; in particular embodiments, the combinations of scavenging agents are histidine and trehalose, histidine and sucrose, glycine and sucrose, histidine, glycine and sucrose, or histidine and tryptophan. In some embodiments, the microparticle formulations containing an active agent, a counterion and a scavenging agent as provided herein can further be tailored to a desired predetermined particle size and uniform size distribution by applying a constant, fixed cooling rate to the feedstock solution for cooling the feedstock solution from a temperature above or at 25° C. to a predetermined temperature below 25° C., whereby microparticles are formed. Additional parameters or steps that can be used to obtain a desired particle size and/or size distribution can include one or more of the following: (1) the concentration of the active agent in the feedstock solution; (2) the nature and/or concentration of the counterion in the feedstock solution; (3) the nature and/or concentration of the organic solvent in the feedstock solution; (4) the concentration of excipient; (5) the volume of feedstock solution in the lyophilization trays; and (6) one or more controlled temperature ramping (temperature decreasing and/or temperature increasing) steps for forming and isolating the resulting microparticles.

Also provided herein are microparticles of a protein containing between about 50% to about 85% wt/wt of the protein, about 2% to about 6% wt/wt of a counterion selected from among citric acid/citrate, magnesium sulfate, potassium sulfate or calcium sulfate, phosphate, pivalate, rubidium, bromine, perchlorate, itaconate, and any salt, acid, or base form thereof, and about 8% to about 40% wt/wt of one or more scavengers. In some embodiments, the protein component of the microparticles can be comprised of a single first polypeptide. In some embodiments, the protein component of the microparticles can be comprised of a single yet different second polypeptide and being the same protein as the first polypeptide. In another embodiment, the protein component of the microparticles can be comprised of a composition of the first polypeptide and the second polypeptide. In one embodiment, the protein is DAS181 (SEQ ID NO:1 or SEQ ID NO:2 or a batch with polypeptides comprising SEQ ID NO:1 and polypeptides comprising SEQ ID NO:2) and in further embodiments, the scavenging agent is present in about 9% to about 11% wt/wt of the dry powder microparticles. In some embodiments, the scavenging agent(s) present in the DAS181 microparticle formulations is histidine, histidine/histidine HCl, histidine/trehalose, histidine/tryptophan, histidine/sucrose, glycine/sucrose, or histidine/glycine/sucrose.

In the methods provided herein, the microparticle formulation of the protein can also be tailored to a desired predetermined particle size and uniform size distribution by modifying one or more additional parameters or steps, including one or more of the following: (1) the concentration of the protein in the feedstock solution; (2) the nature and/or concentration of the counterion in the feedstock solution; (3) the nature and/or concentration of the organic solvent in the feedstock solution; (4) the concentration of excipient; (5) the volume of feedstock solution in the lyophilization trays; and (6) one or more controlled temperature ramping (temperature decreasing and/or temperature increasing) steps for forming and isolating the resulting microparticles.

The methods provided herein for making microparticle formulations can include additional steps. For example, after cooling the feedstock solution at a constant, fixed rate to a predetermined temperature below about 25° C. for forming the microparticles, the cooled solution can be held at that predetermined temperature for a specified period of time to remove unincorporated components of the microparticles by freeze-drying. The microparticles can further be heated in primary and optionally secondary drying steps to remove volatile components by sublimation. In some embodiments, the resulting microparticles are further packaged into materials containing formaldehyde and/or other aldehydes, such as hydroxypropyl methylcellulose (HPMC), aluminum foil laminates, gel capsules or pullulan polysaccharide.

E. Microparticle Formulations that are Stable in their Packaging

Also provided herein are microparticle formulations that are packaged in materials containing formaldehyde and/or other aldehydes. Such materials include, but are not limited to, hydroxypropyl methylcellulose (HPMC) capsules, certain gel capsules, aluminum foil laminate blister packs and pullulan polysaccharide capsules.

Also provided herein are articles of manufacture that contain a microparticle formulation that includes a sialidase or a sialidase fusion protein in an amount of about 60% to about 75% wt/wt, a counterion and a scavenging agent that is a primary amine in the amount of about 8% to about 11% wt/wt, a packaging material for the formulation, where the material contains formaldehyde and/or other aldehydes, and a label that indicates that the composition is for a therapeutic indication. In one embodiment, the therapeutic indication is influenza. In other embodiments, the therapeutic indication is asthma or COPD. In yet other embodiments, the therapeutic indication is selected from among parainfluenza, RSV, sinusitis, otitis, laryngitis, bronchitis, pneumonia, bronchiectasis, vasculitis, mucous plugging, Wegener's granulomatosis and cystic fibrosis (CF). In some embodiments, the scavenging agent is histidine; in other embodiments, the scavenging agent is a combination of histidine and trehalose. In yet other embodiments, the counterion is selected from among citric acid/citrate, magnesium sulfate, potassium sulfate or calcium sulfate, phosphate, pivalate, rubidium, bromine, perchlorate, itaconate, and any salt, acid, or base form thereof. The packaging material can be a HPMC capsule; in further embodiments, the HPMC capsule is clear. In other embodiments, the packaging material can be a gel capsule, or a pullulan polysaccharide capsule. In yet other embodiments, the article of manufacture further contains a secondary packaging material; in some embodiments, the secondary packaging material is a foil laminate; in particular embodiments, the foil laminate is a cold form foil aluminum laminate blister pack. In some embodiments, the scavenging agent is an amine; in further embodiments, the amine is selected from among lysine, histidine, glycine, arginine, glutamine, glutamic acid, cysteine, alanine, tyrosine, tryptophan, aminoguanidine, cysteamine, serine, carnosine, hydralazine and poly(1-lysine). In one embodiment, the sialidase fusion protein is DAS181 having the sequence set forth in SEQ ID NO:1 or SEQ ID NO:2 or a batch with polypeptides comprising SEQ ID NO:1 and polypeptides comprising SEQ ID NO:2; in a particular embodiment, the sialidase fusion protein is DAS181 having the sequence set forth in SEQ ID NO:1 or SEQ ID NO:2 or a batch with polypeptides comprising SEQ ID NO:1 and polypeptides comprising SEQ ID NO:2 and the scavenging agent is histidine or a combination of histidine and trehalose.

The articles of manufacture provided herein also can contain an inhaler for pulmonary administration of the composition. In certain embodiments, the inhaler is a dry powder inhaler, a metered dose inhaler or an electrostatic delivery device.

The microparticles obtained by the methods provided herein are useful as prophylactic, therapeutic or diagnostic agents for treating or diagnosing disease states in a subject in vivo or in vitro.

Active Agents

In some embodiments of the methods and formulations provided herein, the active agents are proteins, including therapeutic proteins such as DAS181 (the sialidase fusion protein having the sequence of amino acid residues set forth in SEQ ID NO:1 or SEQ ID NO:2 a mixture thereof).

Microparticle formulations of other sialidase fusion proteins, besides DAS181, also are contemplated herein. Sialidase-GAG fusion proteins such as DAS181 are proteins that are made up of a sialidase protein, or catalytically active portion thereof, fused to a glycosaminoglycan (GAG)-binding sequence. As such, these proteins effectively contain an anchoring domain (the GAG-binding sequence) and a therapeutic domain (the sialidase protein, or catalytically active portion thereof). The sialidase-GAG fusion proteins are designed to bind to the epithelium and remove the surrounding sialic acids, and can therefore be used as a therapeutic agent against pathogens that utilize sialic acids in the infection process. The ability of the fusion protein to bind to the epithelium increases its retention when the fusion protein is administered, for example, as an inhalant to treat influenza infection. The GAG-binding sequence acts as an epithelium-anchoring domain that tethers the sialidase to the respiratory epithelium and increases its retention and potency.

Counterion

The selection and characterization of counterions has been described extensively elsewhere and is incorporated by reference herein (see, e.g., published U.S. Applications Serial Nos. 20070190163 A1 and its continuation, 20100166874 A1, both of which are titled "Technology for Preparation of Macromolecular Microparticles" and published U.S. Application Serial No. 20090098207 A1 titled "Technology for the Preparation of Microparticles"). The counterions magnesium sulphate and citric acid or citrate, when used in the methods provided herein, can produce microparticles that are of a size that is suitable for administration of a drug to the respiratory tract while avoiding significant absorption into the bloodstream.

Nature and Concentration of Organic Solvent

An organic solvent added to the cocktail in the methods provided herein generally is not a polymer, generally can be water miscible and is selected from among alcohols as described elsewhere and incorporated by reference herein (see, e.g., published U.S. Applications Serial Nos. 20070190163 A1 and its continuation, 20100166874 A1, both of which are titled "Technology for Preparation of Macromolecular Microparticles" and published U.S. Application Serial No. 20090098207 A1 titled "Technology for the Preparation of Microparticles"). In some embodiments of the methods provided herein, the organic solvent is isopropanol. In general, the organic solvent isopropanol is a good solvent of choice because (1) it is a class 3 solvent (i.e., safe), (2) it can produce microspheres in a wide range (2-30%, v/v) of concentrations, and (3) it has a relatively high freezing point so its vapors can efficiently be trapped during lyophilization. In particular embodiments of the methods provided herein, the final concentration of isopropanol is 25% or 26%.

Cooling Ramp

The feedstock solutions from which microparticles are formed according to the methods provided herein are cooled at a constant, fixed preset rate—beginning at a temperature of above or at 25° C. at which the feedstock solution initially is present, and ending at a predetermined temperature below about 25° C. at which the microparticles are formed. The predetermined temperature at which microparticles are formed is empirically determined based on the type of macromolecule, solvents, counterions and other ingredients as well as the rate of cooling and can vary from about or at 15° C., 10° C., 8° C., 5° C., 3° C., 2° C., 1° C., −2° C., −5° C., −7.5° C., −10° C., −15° C., −20° C., −25° C., −30° C., −35° C., −40° C., −45° C., −50° C. or −55° C.

The rate at which cooling and freezing of the cocktail (cooling ramp) is performed can determine the final size of the microparticles. In general, a faster cooling ramp yields smaller microparticles whereas a slower cooling ramp yields larger microparticles. In the methods provided herein, the cooling rates generally are selected to produce microparticles that are larger than about 3 microns and smaller than about 11 microns. Depending on the size of microparticles desired and the type of active agent, the cooling rate can be from about 0.01° C./min to about 1° C./min. In general, the cooling rate is less than 1° C./min and is about 0.3, 0.4, 0.5, 0.6, 0.7 or 0.8° C./min. In some embodiments, the cooling rate is 0.4 C/min or 0.5 C/min.

Scavenging Agents

Microparticle formulations of several active agents or drugs containing amine groups, exemplary of which is the protein DAS181, often are packaged in containers that have components, such as aldehydes, which can react with amine groups present on the active agents, thereby forming cross-linked aggregates and affecting their activity. Exemplary packaging materials that are known to contain aldehydes, either inherently or as a by-product of their formation include hydroxypropyl methyl cellulose (HPMC) capsules and aluminum foil laminates. The manufacture of HPMC includes a step of methyl cellulose reacting with propylene oxide to produce hydroxypropyl methyl cellulose. Without being bound by any theory, during this process, propylene oxide can react with hydroxide to form formaldehyde and acetaldehyde. The aldehydes, as volatile compounds, can leach from HPMC capsules and contact the encapsulated materials (e.g., an API like DAS181). Upon contact, the aldehydes, even when present in trace amounts, (e.g., 10-20 ppm per HPMC capsule) can react with amine groups of the API, resulting in modification and crosslinking of the API and compromising its activity over time. The damaging effect of aldehydes may be enhanced (catalyzed) by other compounds/conditions present in the product and/or packaging such as certain metals (counterions or excipients), moisture and temperature. Therefore, provided herein are methods of making microparticle formulations in which the crosslinking/aggregating effect of aldehydes on the pharmaceuticals/nutraceuticals is reduced or eliminated. In embodiments of the method, the active agent is a protein; in some embodiments, the protein is selected from among sialidases, sialidase fusion proteins, proteases, protease inhibitors, cytokines, insulin, BSA, human growth hormone, calcitonin, recombinant human DNase, interferons and parathyroid hormone; in yet other embodiments, the protein is a sialidase fusion protein. In a particular embodiment, the sialidase fusion protein is DAS181 having the sequence set forth in SEQ ID NO:1. In another particular embodiment, the sialidase fusion protein is DAS181 having the sequence set forth in SEQ ID NO:2. In another particular embodiment, the sialidase fusion protein is DAS181 and is present as a batch with polypeptides comprising SEQ ID NO:1 and polypeptides comprising SEQ ID NO:2. In yet another particular embodiment, the sialidase fusion protein is DAS181 and the scavenging agent is histidine. In further embodiments, the sialidase fusion protein is DAS181 and the scavenging agent is a mixture of histidine and trehalose, histidine and tryptophan, tryptophan alone, glycine alone, glycine and sucrose, glycine, histidine and sucrose, or histidine and sucrose.

Other exemplary drugs or active agents containing amine groups that can be shielded from packaging material (aldehyde)-mediated cross-linking and/or degradation by forming drug microparticles containing a scavenging agent include, but are not limited to, sialidases, sialidase fusion proteins, proteases, protease inhibitors, cytokines, insulin, BSA, human growth hormone, calcitonin, recombinant human DNase, interferons, parathyroid hormone, exenatide-4, α-synuclein and known small molecule drugs such as the proton pump inhibitor Nexium® (esomeprazole magnesium; Astra Zeneca), the antiviral Valtrex® (valacyclovir hydrochloride; Glaxo SmithKline), the anticonvulsant Lyrica® (pregabalin; Pfizer), the anti-inflammatory drug Asacol® (mesalamine; Proctor & Gamble), the antihistamine Clarinex® (desloratadine; Schering Plough), the dopamine agonist Mirapex® (pramipexole; Boehringer Ingelheim) and the antiviral Zovirax® (acyclovir; Glaxo SmithKline).

The methods provided herein for stabilization of the active agents (pharmaceuticals/nutraceuticals) against the damaging effect of aldehydes include adding a scavenging agent to the feedstock solution whereby the scavenging agent is incorporated into the resulting microparticle formulations containing the active agents. Exemplary scavenging agents include, but are not limited to, primary and secondary amines, chelators, antioxidants, sugars and combinations thereof.

In some embodiments, the scavenging agent is a primary or secondary amine. Without being bound by any theory, the amine could act as a scavenging agent by reacting with the aldehyde, thereby protecting the amine groups of the active agent from reacting with the aldehyde. In further embodiments, the primary or secondary amine is selected from among lysine, histidine, glycine, arginine, glutamine, glutamic acid, cysteine, alanine, tyrosine, tryptophan, aminoguanidine, cysteamine, serine, carnosine, hydralazine and poly(1-lysine). In yet other embodiments, the amine is histidine. Without being bound by any theory, the reaction of histidine with an aldehyde such as formaldehyde can form the product spinacine, which is known to be non-toxic and therefore is less likely to pose a health risk when administered in a microparticle formulation containing an API. In exemplary microparticle formulations containing an amine as a scavenging agent, the concentrations of the amino acids in the dry powder are between about 0.5% and about 20% w/w.

In other embodiments, the scavenging agent is an antioxidant. Exemplary antioxidants that can inhibit oligomer formation and destabilization of proteins such as DAS181 include, but are not limited to, ascorbic acid and its derivatives (such as substituted compounds at 2-, 3-, 5- and 6-positions including L-ascorbate-2-sulphate and L-ascorbate-2-phosphate, L-ascorbyl-6-palmitate), thioglycerol, glutathione, tocopherol, melatonin, sodium bisulfite, urea, ethylene urea, 3,4-diaminobenzoic acid, allantoin, glycouril, anthranilic acid, methyl anthranilate, methyl 4-aminobenzoate, ethyl acetoacetate, acetoacetamide, malonamide, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, glucose, cellulose, poly(vinyl alcohol), partially hydrolyzed poly(vinylformamide), poly(vinyl amine), poly (ethylene imine), poly(oxyalkyleneamine), poly(vinyl alcohol)-co-poly(vinyl amine), poly(4-aminostyrene), poly (l-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, ammonium hydroxide, benzylamine, hydroxycitronellol, cyclohexanone, 2-butanone, pentane dione, dehydroacetic acid and mixtures thereof.

In the case of ascorbate derivatives, when the active agent is a protein, it is thought that these compounds react with ϵ-amino groups of L-lysine residues on the protein, thereby reducing the number of active sites on the protein that can react with aldehydes such as formaldehyde that are present in the packaging container/capsule. The ascorbate derivatives can also contain amino groups, thereby providing an additional mechanism for reacting with the aldehydes and protecting the active agents from their damaging effects. Exemplary derivatives that include amine functionalities include L-ascorbic acid derivatives are selected from the group consisting of ascorbyl-6-lysine, ascorbyl-2-lysine, ascorbyl-6-polylysine, ascorbyl-2,6-dilysine, ascorbyl-6-polylysine-2-lysine, ascorbyl-6-lysine-2-polylysine, ascorbyl-2,6-polylysine, ascorbyl-6-proline, ascorbyl-2-proline, ascorbyl-6-polyproline, ascorbyl-2-polyproline, ascorbyl-2,6-diproline, ascorbyl-2-proline-6-polyproline, ascorbyl-2-polyproline-6-proline, ascorbyl-2,6-diproline, 6-deoxyascorbyllysine, 6-deoxyascorbylproline, 6-deoxyascorbylpolylysine, 6deoxyascorbylpolyproline, 6-deoxyascorbyllysine-2-proline, 6-deoxyascorbylproline-2-lysine, 6-deoxyascorbylpolylysine-2-proline, 6-deoxyascorbylpolyproline-2-lysine, 6-deoxyascorbyllysine-2-polyproline, 6-deoxyascorbylproline-2-polylysine, 6-deoxyascorbate proline-2-lysine-proline, 6-deoxyascorbate-2-proline-lysine, 6-deoxyascorbyllysine, 6-deoxyascorbate-lysine-proline, 6-deoxyascorbyl-lysine-2-proline, 6-deoxyascorbyl-polylysine-2-proline, 6-deoxyascorbyl-lysine-2-polyproline, 6-deoxyascorbyl-lysine-2lysine-proline, 6-deoxyamino ascorbyl-polylysine, 6-deoxyamino ascorbyl-lysine-proline, 6-deoxyamino ascorbylproline and 6-deoxyamino ascorbylpolyproline.

In yet other embodiments, the scavenging agent is a chelator. An exemplary chelator is triethylenetetramine (TETA), which can be efficacious in preventing protein oligomer formation due to the presence of four amine groups that can act as formaldehyde/aldehyde scavenger or a chelator. Histidine or tryptophan could also function as chelators. Other chelators that can act as scavenging agents in concert with primary and/or secondary amines include diethylenetriamine pentaacetic acid (DTPA) and metal-based (e.g., copper, iron, manganese) chelating agents In further embodiments, sugars added to the microparticle formulations provided herein can inhibit the active agent oligomerization/aggregation that can occur in the presence of aldehydes such as formaldehyde. Without being limited by any particular mechanism, when the active agent is a protein such as DAS181, the reduction of aggregation in presence of sugar could be attributed to the sugars forming hydrogen-bonds with the available sites on the protein surface, thereby reducing access of the aldehydes to the amine groups on the protein. Sugars such as trehalose and sucrose may also stabilize the tertiary structure of the protein, thereby providing better stability against thermal activation. The final concentrations of sugars in the dry microparticle formulations can be between about 1% and about 15% w/w. Thus, in some embodiments of the methods provided herein, a combination of a primary amine, such as histidine, and a sugar, such as trehalose, are added to the feedstock solution for incorporation into the microsphere formulations to provide added stability to the formulations.

Optional Additional Agents

The compositions provided herein can optionally, in addition to an active agent, contain one or more surfactant and/or additional pharmaceutical or nutraceutical or other such agent for ingestion by a subject; such additional agents and their characteristics and proportions in the microparticle formulations are described extensively in U.S. Applications Serial Nos. 20070190163 A1 and its continuation, 20100166874 A1, both of which are titled "Technology for Preparation of Macromolecular Microparticles" and in published U.S. Application Serial No. 20090098207 A1 titled "Technology for the Preparation of Microparticles," all of which are incorporated by reference herein.

F. Uses of the Compositions

Therapeutic and diagnostic applications of the microparticles can include drug delivery, vaccination, gene therapy, and in vivo tissue or tumor imaging. Routes of administration can include oral or parenteral administration; mucosal administration; ophthalmic administration; intravenous, subcutaneous, intra-articular, or intramuscular injection; inhalation administration; and topical administration. In particular embodiments, the microparticles are suitable for pulmonary administration by inhalation for the prevention, prophylaxisor treatment of diseases of the respiratory tract including influenza, parainfluenza, RSV, sinusitis, otitis, laryngitis, bronchitis, pneumonia, allergic and non-allergic asthma, COPD, bronchiectasis, vasculitis, mucous plugging, Wegener's granulomatosis and cystic fibrosis (CF).

The microparticle formulations provided herein can be formulated as tablets, caplets, gels, vials, pre-filled syringes, inhalers, electrostatic devices and other devices for delivery. In some embodiments, the packaging materials used to package the formulations contain formaldehyde or other aldehydes; exemplary materials include HPMC, certain gels, aluminum foil laminates and pullulan polysaccharides. The delivery dosage of the formulations can be from between about 0.5 mg protein per dose to about 100 mg protein per dose, or about 0.75 mg, 1 mg, 1.5 mg, 2 mg, 3 mg, 5 mg, 10 mg, 15 mg, 20 mg, 30 mg, 40 mg, 45 mg, 50 mg, 55 mg or 60 mg protein per dose. The frequency and amount of administration of a dose, for example, for the treatment or prophylaxis of influenza or asthma using DAS181, can be from three or more times a day, to two times a day, to once a day, to two times a week, to once a week, to once every two weeks or less frequent than once every two weeks. In some embodiments for the treatment of influenza, parainfluenza or asthma, the delivery dose of a DAS181 (SEQ ID NO:1 or SEQ ID NO:2 or a batch with polypeptides comprising SEQ ID NO:1 and polypeptides comprising SEQ ID NO:2) microparticle formulation by inhalation is 10 mg; in particular administrations, 13 mg of Formulation A filled in a #3 clear HPMC capsule (delivered dose of 10 mg) is administered once a day for the treatment of influenza, parainfluenza or asthma, and in further embodiments the administration can be for up to 3 consecutive days.

Packaging of the Dry Powder

The dry microparticle formulation was packaged in a primary container closure system that is a natural (clear), Size 3, HPMC capsule (Capsugel). The dry powder fill mass for each capsule was about 11 mg to achieve a 10 mg delivered dose. The packaged HPMC capsules were then put into a cold form aluminum laminate blister pack as a secondary container closure system

EXAMPLE 1

Manufacture of Uniform Stable Microparticles of DAS181 with Magnesium Sulfate as the Counterion and Histidine as the Scavenging Agent A. Purification of DAS181

DAS181 is a fusion protein containing the heparin (glysosaminoglycan, or GAG) binding domain from human amphiregulin fused via its N-terminus to the C-terminus of a catalytic domain of *Actinomyces Viscosus* (e.g., SEQ ID NO: 1 (without amino terminal methionine) and SEQ ID NO: 2 (with amino terminal methionine)). The DAS181 protein used in the examples below was purified as described in Malakhov et al., *Antimicrob. Agents Chemother.,* 1470-1479 (2006), which is incorporated in its entirety by reference herein. Briefly, the DNA fragment coding for DAS181 was cloned into the plasmid vector pTrc99a (Pharmacia) under the control of a IPTG (isopropyl-β-D-thiogalactopyranoside)-inducible promoter. The resulting construct was expressed in the BL21 strain of *Escherichia Coli* (*E. Coli*). The *E. coli* cells expressing the DAS181 protein were washed by diafiltration in a fermentation harvest wash step using Toyopearl buffer 1, UFP-500-E55 hollow fiber cartridge (GE Healthcare) and a Watson-Marlow peristaltic pump. The recombinant DAS181 protein was then purified in bulk from the cells as described in published U.S. Applications Serial Nos. 20050004020 A1 and 20080075708 A1, which are incorporated in their entirety by reference herein.

B. Activity of DAS181

The sialidase activity of DAS181 was measured using the fluorogenic substrate 4-methylumbelliferyl-N-acetyl-α-D-neuraminic acid (4-MU-NANA; Sigma). One unit of sialidase is defined as the amount of enzyme that releases 10 nmol of MU from 4-MU-NANA in 10 minutes at 37° C. (50 mM $CH_3COOH$—NaOH buffer, pH 5.5) in a reaction that contains 20 nmol of 4-MU-NANA in a 0.2 ml volume (Potier et al., *Anal. Biochem.,* 94:287-296, 1979). The specific activity of DAS181 was determined to be 1,300 U/mg protein (0.77 μg DAS181 protein per unit of activity).

C. Batch Mode Process and Formulation of DAS181 Microparticles

The following ingredients were combined to form DAS181 microparticles in a large scale batch process:

(a) 75 mg/ml Histidine, pH 6.0, 1 M Trehalose, 1.25 M magnesium sulfate and 100 mM calcium chloride stock solutions were sterile filtered into and combined in an Excipient Bottle.

(b) The contents of the Excipient Bottle were added, with mixing, to a Compounding Vessel containing 125 mg/ml DAS181 protein prepared as described above.

(c) Isopropanol was sterile filtered into an Isopropanol Bag (d) The content of the Isopropanol Bag was pumped into the Compounding Vessel while mixing vigorously to form the Feedstock Solution. The final composition of the Feedstock Solution was as follows: 70 mg/ml DAS181, 25% isopropanol, 10.5 mg/ml histidine, 10.5 mg/ml trehalose, 5.06 mg/ml magnesium sulfate, 0.19 mg/ml calcium chloride, pH 6.0. The time between initiating the addition of isopropanol and starting the lyophilization cycle was between 90 minutes and 120 minutes (e) Stainless Steel trays that had undergone depyrogenation were each filled with 950 g of the Feedstock Solution, using a metering pump (f) The filled Stainless Steel trays were subsected to a Lyophilization Cycle as follows:

a. the trays were gasketed and placed in the lyophilizer shelves at 25° C. for 5 minutes;

b. the temperature of the shelves was lowered to −55° C. at a ramp rate of −0.5° C./minute;

c. the trays were held at −55° C. for between 60 and 180 minutes;

d. primary drying was accomplished by setting the condenser to <−60° C., applying a vacuum of 125 mTorr and increasing the temperature to −40° C. at a ramp rate of 0.125° C./minute and further to a temperature of −25° C. at 0.25° C./minute;

e. the temperature was held at −25° C. for between 5000 and 6500 minutes;

f. secondary drying was accomplished by increasing the temperature to 15° C. at a ramp rate of 0.67°

C./minute and further to a temperature of 30° C. at a ramp rate of 0.5° C./minute;

g. the temperature was held at 30° C. for between 300 and 500 minutes; and h. the vacuum was released and the lyophilizer was backfilled with nitrogen to prevent oxidation of the microparticle formulation before transferring into bottles for bulk mixing and aliquoting the bulk powder for storage at ≤−15° C.

Transfer of Bulk DAS181 Microparticles into Container and Mixing

A section on the bottom film of each Stainless Steel tray was cleaned using sanitizing wipes and a 3×3 cm opening was made with a scalpel. The dry microparticles were transferred into a plastic bottle. The bottle was capped and tumbled forty times, changing directions with each inversion. The tumbling was to ensure uniformity of bottle content. Samples for analytical testing were taken and the bottle was recapped and sealed into plastic bags for storage at ≤−15° C.

Dry Powder Composition and Properties (Formulation II Example)

The DAS181 microparticle formulation dry powder, prepared according to the method described above as the following composition and physical parameters:

| Composition (wt/wt %): | |
|---|---|
| DAS181: | 64.5-64.7% |
| Histidine free base: | 4.3-4.6% |
| Histidine HCl: | 5.9-6.3% |
| Trehalose: | 9.1-9.7% |
| Magnesium sulfate: | 4.7-5.8% |
| Calcium chloride: | 0.2% |
| Sodium acetate (trace amounts from DAS181 stock solution): | 0.04-0.05% |
| Acetic acid (trace amounts from DAS181 stock solution): | 0.02% |
| Water: | 10% |
| Isopropanol: | trace amounts |

Physical Parameters:

The DAS181 dry powder microparticles prepared according to the above method have a mass median aerodynamic diameter (MMAD) of 6.4 microns, a GSD of 1.4-1.6, an FPF of 0.9-2.1% for particle sizes <3.2 microns and an FPF of 8.9-10.7% for particle sizes <5 microns.

The suitability of the microparticles for administration by oral inhalation to treat respiratory tract infections such as influenza was tested by Andersen Cascade Impaction. The deposition of pharmaceuticals in the respiratory tract can be predicted by deposition of particles (microparticles) on the stages/collection plates of the cascade impactor. For the DAS181 microparticles, when administered to prevent or treat viral infections that initiate in the respiratory tract, such as influenza, it is desirable to deposit the drug in the throat, trachea and bronchi (upper respiratory airway) while avoiding deposition at the secondary and terminal bronchi and the alveoli. The results showed that only about 1.2% of the microparticles were deposited at the collection plates corresponding to secondary and terminal bronchi and the alveoli, with about 0.2% being deposited at the alveoli.

Packaging of the Dry Powder

The dry microparticle formulation was packaged in a primary container closure system that is a natural (clear), Size 3, HPMC capsule (Capsugel). The dry powder fill mass for each capsule was about 13 mg to achieve a 10 mg delivered dose. The packaged HPMC capsules were then put into a cold form aluminum laminate blister pack as a secondary container closure system

EXAMPLE 2

Manufacture of Uniform Stable Microparticles of DAS181 with Citric Acid/Citrate as the Counterion and Histidine as the Scavenging Agent The DAS181 protein was purified and its activity measured as described in Example 1 (Sections 1A and 1B). The following ingredients were then combined to form DAS181 microparticles in a large scale batch process:

(a) 75 mg/ml Histidine, 0.107M citric acid, pH 5.0 and 1M Trehalose stock solutions were sterile filtered into and combined in an Excipient Bottle.

(b) The contents of the Excipient Bottle were added, with mixing, to a Compounding Vessel containing 125 mg/ml DAS181 protein prepared as described in Example 1.

(c) Isopropanol was sterile filtered into an Isopropanol Bag (d) The content of the Isopropanol Bag was pumped into the Compounding Vessel while mixing vigorously to form the Feedstock Solution. The final composition of the Feedstock Solution was as follows: 70 mg/ml DAS181, 26% isopropanol, 9.8 mg/ml histidine, 9.8 mg/ml trehalose, 2.69 mg/ml citric acid, pH 5.0. The time between initiating the addition of isopropanol and starting the lyophilization cycle was between 90 minutes and 120 minutes (e) Stainless Steel trays that had undergone depyrogenation were each filled with 950 g of the Feedstock Solution, using a metering pump (f) The filled Stainless Steel trays were subjected to a Lyophilization Cycle as follows:

a. the feedstock solution in the lyophilization trays were gasketed and placed in the lyophilizer shelves at 25° C. for 5 minutes;

b. the temperature of the shelves was lowered to −55° C. at a ramp rate of −0.4° C./minute;

c. the trays were held at −55° C. for between 60 and 180 minutes;

d. primary drying was accomplished by setting the condenser to <−60° C., applying a vacuum of 125 mTorr with 250 mTorr dead band and increasing the temperature to −40° C. at a ramp rate of 0.125° C./minute and further to a temperature of −30° C. at 0.167° C./minute;

e. the temperature was held at −30° C. for between 5000 and 6500 minutes;

f. secondary drying was accomplished by increasing the temperature to 15° C. at a ramp rate of 0.5° C./minute, holding at 15° C. for 30 minutes, then further ramping up to a temperature of 30° C. at a ramp rate of 0.5° C./minute;

g. the temperature was held at 30° C. for between 300 and 500 minutes; and h. the vacuum was released and the lyophilizer was backfilled with nitrogen to prevent oxidation of the microparticle formulations before transferring into bottles for bulk mixing and aliquoting the bulk powder for storage at ≤−15° C.

Transfer of Bulk DAS181 Microparticles into Container and Mixing

A section on the bottom film of each Stainless Steel tray was cleaned using sanitizing wipes and a 3×3 cm opening was made with a scalpel. The dry microparticles were transferred into a plastic bottle. The bottle was capped and tumbled forty times, changing directions with each inversion. The tumbling was to ensure uniformity of bottle content. Samples for analytical testing were taken and the bottle was recapped and sealed into plastic bags for storage at ≤−15° C.

Dry Powder Composition and Properties

The DAS181 microparticle formulation dry powder, prepared according to the method described above as the following composition and physical parameters:

| Composition (wt/wt %): | |
|---|---|
| DAS181 | 70.15% |
| Histidine free base: | 6.08% |
| Histidine HCl: | 3.92% |
| Trehalose: | 9.25% |
| Citric acid: | 2.54% |
| Sodium acetate (trace amounts from DAS181 stock solution): | 0.04% |
| Acetic acid (trace amounts from DAS181 stock solution): | 0.02% |
| Water: | 8% |
| Isopropanol: | trace amounts |

Physical Parameters:

The DAS181 dry powder microparticles prepared according to the above method have a mass median aerodynamic diameter (MMAD) of 10.4 microns, a GSD of 1.6 and an FPF of 2.1% for particle sizes <5 microns.

The suitability of the microparticles for administration by oral inhalation to treat respiratory tract infections such as influenza was tested by a Next Generation Impactor. The deposition of pharmaceuticals in the respiratory tract can be predicted in a manner similar to that of Andersen Cascade Impaction, by deposition of particles (microparticles) on the stages/collection plates of the cascade impactor. For the DAS181 microparticles, when administered to prevent or treat viral infections that initiate in the respiratory tract, such as influenza, it is desirable to deposit the drug in the throat, trachea and bronchi (upper respiratory airway) while avoiding deposition at the secondary and terminal bronchi and the alveoli. The results showed that only about 1% of the microparticles were deposited at the collection plates corresponding to secondary and terminal bronchi and the alveoli, with no detectable microparticles at the collection plates corresponding to alveoli.

Packaging of the Dry Powder

The dry microparticle formulation was packaged in a primary container closure system that is a natural (clear), Size 3, HPMC capsule (Capsugel). The dry powder fill mass for each capsule was about 11 mg to achieve a 10 mg delivered dose. The packaged HPMC capsules were then put into a cold form aluminum laminate blister pack as a secondary container closure system.

EXAMPLE 3

HPMC Capsules and DAS181 Microparticles Exposed to HPMC Capsules Contain Formaldehyde A. Qualitative Assay to Detect Aldehyde in HPMC Capsules and Dry Powder DAS181 Microparticle Formulations The presence of aldehyde in a sample can qualitatively be detected by a colorimetric assay 4-amino-5-hydrazino-1, 2, 4-triazole-3-thiol (AHTT) (Rahn, C. H. et al., *Lipids,* 8(11): 612-616 (1973)). AHTT or purpald, when in basic solution, turns purple in the presence of aldehyde. In the absence of aldehyde, the AHTT in basic solution remains slightly pinkish. The following samples were evaluated by colorimetric method:

(1) DAS181 microparticle formulations not exposed to HPMC capsules and containing no detectable dimer (2) DAS181 microparticle formulations stored in HPMC capsules for 12 weeks at 37° C. and known to have dimer content as determined by size exclusion HPLC (SE-HPLC or SEC)

(3) HPMC capsules used to package the DAS181 microparticle formulations (#3, clear) that have never been in contact with DAS181 microparticle formulations (4) formaldehyde as a positive control.

The results showed that only samples (2), (3) and (4) turned purple when reacted with AHTT. Thus, HPMC capsules contain aldehyde (sample (3)) and DAS181 dry powder microparticle formulations, when stored in HPMC capsules, absorb the aldehyde that leaches from the HPMC containers (sample (2)). The DAS181 powder that never was in contact with HPMC capsules (sample (1)) does not contain detectable amounts of aldehyde. HPMC capsule itself also contains aldehyde groups that can react with AHTT (sample (3)).

B. Formaldehyde Detection in HPMC Capsules: Quantitative Assay

The presence of extractable (leached) formaldehyde in HPMC capsules was identified and quantitated by GC spectroscopy. The ratio of formaldehyde to cyclohexanone internal standard was used to quantitate the extractable formaldehyde. 2, 3, 4, 5, 6-pentafluorobenzyloxamine (PFBOA) in presence of a 1% potassium hydrogen phthalate was used as a derivatizing agent.

Results from extraction of formaldehyde from HPMC capsules were reproducible in the range of 1-15 ppm formaldehyde extracted. Formaldehyde content in different capsule lots was age-dependent. Pretreatment of capsules by storing them at 40° C. and 75% RH (relative humidity) before the analysis lowered the amount of extractable formaldehyde.

EXAMPLE 4

Oligomer Formation of DAS181 in Microparticles Stored in HPMC Capsules

A. Measurement of Dimer and Higher Order Oligomer Formation

SDS-PAGE

The stability of DAS181 polypeptides in dry powder microparticles stored in HPMC capsules was tested by assaying for the presence of DAS181 dimers and higher order oligomers formed by reacting with formaldehyde from the HPMC capsules over time. The DAS181 dimers and higher order oligomers can be detected qualitatively by their differential migration on a gel relative to the monomer, as measured by SDS-PAGE. The molecular weight of DAS181 is about 45 kDa; however, due to the presence of the positively charged amphiregulin GAG-binding domain, the DAS181 monomer band generally migrates at around 48 to 50 kDa. When dimerization of DAS181 occurs, two dimer bands at around 100 kDa and around 120 kDa, respectively are observed. Higher order oligomers of DAS181 often stay in the well and can be detected as aggregates in the well. Thus, the stability of the DAS181 monomer in microparticle formulations can be visualized qualitatively by SDS-PAGE.

SEC

The presence of DAS181 dimers or higher-order oligomers due to reaction of the DAS181 monomer with formaldehyde from the HPMC capsules can be quantitated by SE-HPLC or SEC (size exclusion HPLC), in which the larger dimer elutes first through the resin pores while the smaller DAS181 45 kDa monomer (i.e., un-aggregated, stable form) is retained longer in the smaller pores.

B. Stability of Microparticles in HPMC Capsules

Magnesium Sulfate as Counterion

A microparticle formulation containing magnesium sulfate as counterion, histidine as a scavenging agent and trehalose as an additional stabilizer, was compared against other microparticle formulations whose composition was as follows (composition values were corrected for residual moisture):

| | |
|---|---|
| (1) Control Formulation: | 96.61% DAS181, 3.10% magnesium sulfate, 0.29% calcium chloride. |
| (2) +Histidine*: | 80.04% DAS181, 7.72% magnesium sulfate, 0.24% calcium chloride, 12.01% histidine |
| (3) +Histidine +Trehalose: | 72.71% DAS181, 5.26% magnesium sulfate, 0.22% calcium chloride, 10.91% histidine, 10.91% trehalose |
| (4) +Histidine +Trehalose: +Tryptophan | 71.37% DAS181, 3.44% magnesium sulfate, 0.21% calcium chloride, 10.71% glycine, 3.57% tryptophan, 10.71% trehalose |
| (5) +Glycine +Mannitol: | 75.46% DAS181, 5.45% magnesium sulfate, 0.22% calcium chloride, 7.55% glycine, 11.32% mannitol |

*Histidine/Histidine HCl

Formulations (1) through (5) above were placed in either a "low formaldehyde" HPMC capsule (4 ppm formaldehyde) or a "high formaldehyde" HPMC capsule (8 ppm formaldehyde). The capsules were filled to 5 mg powder and maintained at 37° C. for 12 weeks, at which time their dimer content (%) was measured.

Results: In the "low formaldehyde" HPMC capsules, the % dimer detected at 12 weeks, 37° C. was as follows:

| | |
|---|---|
| (1) Control Formulation: | 6.9% dimer |
| (2) +Histidine: | 1.7% dimer |
| (3) +Histidine +Trehalose: | 1.7% dimer |
| (4) +Histidine +Trehalose: +Tryptophan | 1.5% dimer |
| (5) +Glycine +Mannitol: | 4.8% dimer |

Thus, the presence of histidine in the formulation significantly decreased dimer formation over time and was more effective than the combination of glycine (amine) and mannitol (sugar). While the presence of the sugar trehalose did not appear to enhance the dimer-reducing effect of histidine, trehalose can stabilize the protein against moisture-induced aggregation (see Example 6 below) by increasing the thermal stability of the formulation (due to the high glass transition temperature of trehalose) as well as inhibiting the reaction of free residual moisture with the protein.

Similar results were obtained with the "high formaldehyde" HPMC capsules. At 12 weeks, 37° C., the % dimer detected was as follows:

| | |
|---|---|
| (1) Control Formulation: | 13.9% dimer |
| (2) +Histidine: | 1.7% dimer |
| (3) +Histidine +Trehalose: | 1.5% dimer |
| (4) +Histidine +Trehalose: +Tryptophan | 1.5% dimer |
| (5) +Glycine +Mannitol: | 7.1% dimer |

These results show that the presence of histidine in the DAS181 microparticle formulations significantly reduces DAS181 dimer formation in HPMC capsules and enhances its long-term stability.

Citric Acid as Counterion

The DAS181 microparticle formulation prepared with citric acid as counterion, histidine as a scavenging agent and trehalose as an additional stabilizer showed a protective effect that was comparable to that shown by the microparticle formulation of in the previous example with magnesium sulfate as a counterion. For example, when the samples were stored at 40° C. for 3 months, the percentage of DAS181 monomer in the formulations (i.e., intact drug product) was as follows:

| | |
|---|---|
| Formulation (magnesium sulfate counterion): | 96.4% |
| Formulation (citric acid counterion): | 96.5% |

When stored at 25° C. instead of 40° C., the percentage of DAS181 monomer in the formulations was as follows:

| | |
|---|---|
| Formulation (magnesium sulfate counterion): | 98.2% |
| Formulation (citric acid counterion): | 97.9% |

EXAMPLE 5

Stability of DAS181 Microparticles Containing Various Amines

Microparticle formulations of DAS181 were prepared according to the general method described in Example 1, except that histidine was replaced with various other amino acids as shown below. The dry powder formulations were stored at 37° C. in polypropylene Eppendorf tubes (unencapsulated) or in clear #3 HPMC capsules, and the amount of dimer measured at one month, two months or three months. The results are shown below in Table 1 (dry powder composition values corrected for residual moisture):

TABLE 1

Effect of Amines on DAS181 Dimer Formation in Microparticle Formulations

| Formulation (% wt/wt) | Amino Acid | % Oligomer t = 0 | HPMC Capsules 1 mo | HPMC Capsules 2 mo | HPMC Capsules 3 mo | Unencapsulated 1 mo | Unencapsulated 2 mo | Unencapsulated 3 mo |
|---|---|---|---|---|---|---|---|---|
| 96.96% DAS181, 2.75% sodium sulfate, 0.29% calcium chloride | None | 0.96 | 11.2 | 7.5 | 10.9 | 4.9 | 5.1 | 6.2 |
| 97.37% DAS181, 2.34% magnesium sulfate, 0.29% calcium chloride | None | 0.80 | 9.3 | 5.9 | 8.4 | 3.3 | 3.0 | 4.2 |
| 84.70% DAS181, 2.04% magnesium sulfate, 0.25% calcium chloride, 13.01% histidine | Histidine | 0 | 1.0 | 0.9 | 1.2 | 1.3 | 1.1 | 2.2 |
| 85.18% DAS181, 2.05% magnesium sulfate, 0.26% calcium chloride, 12.52% methionine | Methionine | 0.60 | 7.6 | 11.9 | 14.9 | 2.9 | 3.8 | 3.7 |
| 85.35% DAS181, 2.06% magnesium sulfate, 0.26% calcium chloride, 12.34% glutamic acid | Glutamic Acid | 0 | 4.3 | 3.4 | 3.7 | 1.4 | 1.3 | 2.1 |

TABLE 1-continued

Effect of Amines on DAS181 Dimer Formation in Microparticle Formulations

| Formulation (% wt/wt) | Amino Acid | % Oligomer t = 0 | HPMC Capsules 1 mo | HPMC Capsules 2 mo | HPMC Capsules 3 mo | Unencapsulated 1 mo | Unencapsulated 2 mo | Unencapsulated 3 mo |
|---|---|---|---|---|---|---|---|---|
| 83.19% DAS181, 2.0% magnesium sulfate, 0.25% calcium chloride, 14.55% arginine | Arginine | 0 | 6.0 | 2.3 | 4.5 | 2.2 | 1.3 | 1.9 |
| 91.66% DAS181, 2.21% magnesium sulfate, 0.27% calcium chloride, 5.86% glycine | Glycine | 0 | 4.8 | 2.4 | 3.2 | 3.5 | 2.3 | 2.9 |
| 88.04% DAS181, 2.12% magnesium sulfate, 0.26% calcium chloride, 9.58% proline | Proline | 0 | 5.0 | 3.2 | 4.1 | 1.9 | 1.7 | 1.7 |
| 80.93% DAS181, 1.95% magnesium sulfate, 0.24% calcium chloride, 16.88% tryptophan | Tryptophan | 0.3 | 1.4 | 2.1 | 2.9 | 1.2 | 1.5 | 1.9 |
| 87.86% DAS181, 2.12% magnesium sulfate, 0.26% calcium chloride, 9.76% valine | Valine | 0.4 | 7.8 | 12.1 | 16.1 | 2.3 | 2.8 | 5.2 |
| 90.36% DAS181, 2.18% magnesium sulfate, 0.27% calcium chloride, 7.19% alanine | Alanine | 0.3 | 6.4 | 8.8 | 12.0 | 1.6 | 1.8 | 2.5 |
| 86.67% DAS181, 2.09% magnesium sulfate, 0.26% calcium chloride, 10.98% leucine | Leucine | 0.6 | 7.8 | 12.1 | 14.9 | 3.0 | 3.7 | 4.8 |

TABLE 1-continued

Effect of Amines on DAS181 Dimer Formation in Microparticle Formulations

| Formulation (% wt/wt) | Amino Acid | t = 0 | HPMC Capsules 1 mo | HPMC Capsules 2 mo | HPMC Capsules 3 mo | Unencapsulated 1 mo | Unencapsulated 2 mo | Unencapsulated 3 mo |
|---|---|---|---|---|---|---|---|---|
| 86.67% DAS181, 2.09% magnesium sulfate, 0.26% calcium chloride, 10.98% isoleucine | Isoleucine | 0.5 | 8.1 | 12.1 | 15.3 | 2.7 | 3.8 | 4.6 |

(% Oligomer)

Of the amines tested, histidine and tryptophan were found to be the most effective at preventing DAS181 oligomer formation and increasing the stability of the formulation relative to ones in which no amine is present. It is possible that histidine and tryptophan have a stabilizing chelating effect, in addition to the amine functionality reacting with formaldehyde.

The effect of amine concentration (% wt/wt in dry powder) on DAS181 dimer formation in the microparticle formulation was measured, and the results are shown in Table 2 (composition values corrected for residual moisture):

TABLE 2

Effect of Amine Concentration on DAS181 Dimer Formation in Microparticle Formulations

| Formulation (% wt/wt) | Amino Acid | t = 0 | HPMC Capsules 1 mo | HPMC Capsules 2 mo | Unencapsulated 1 mo | Unencapsulated 2 mo |
|---|---|---|---|---|---|---|
| 97.37% DAS181, 2.34% magnesium sulfate, 0.29% calcium chloride | None | 1.1 | 4.8 | 6.9 | 2.6 | 3.4 |
| 97.232% DAS181, 2.3433% magnesium sulfate, 0.29% calcium chloride, 0.133% histidine | 0.1% Histidine | 1.2 | 3.5 | 4.4 | 2.4 | 3.1 |
| 96.079% DAS181, 2.3155% magnesium sulfate, 0.2882% calcium chloride, 1.3176% histidine | 1.3% Histidine | 1.0 | 2.3 | 3.1 | 2.1 | 2.6 |
| 91.268% DAS181, 2.1996% magnesium sulfate, 0.2738% calcium chloride, 6.2583% histidine | 6.26% Histidine | 0.6 | 1.4 | 1.6 | 1.3 | 1.6 |
| 84.696% DAS181, 2.0412% magnesium sulfate, 0.2541% calcium chloride, 13.009% histidine | 13% Histidine | 0.4 | 0.9 | 1.1 | 0.5 | 1.1 |
| 97.31% DAS181, 2.35% magnesium sulfate, 0.29% calcium chloride, 0.06% glycine | 0.06% Glycine | 1.1 | 4.9 | 6.6 | 2.5 | 3.2 |

(% Oligomer)

TABLE 2-continued

Effect of Amine Concentration on DAS181 Dimer Formation in Microparticle Formulations

| Formulation (% wt/wt) | Amino Acid | t = 0 | HPMC Capsules 1 mo | HPMC Capsules 2 mo | Unencapsulated 1 mo | Unencapsulated 2 mo |
|---|---|---|---|---|---|---|
| 96.82% DAS181, 2.33% magnesium sulfate, 0.29% calcium chloride, 0.55% glycine | 0.55% Glycine | 1.1 | 4.3 | 6.0 | 2.6 | 2.1 |
| 94.73% DAS181, 2.28% magnesium sulfate, 0.28% calcium chloride, 2.70% glycine | 2.7% Glycine | 0.7 | 3.1 | 4.2 | 2.0 | 2.5 |
| 91.66% DAS181, 2.21% magnesium sulfate, 0.27% calcium chloride, 5.86% glycine | 5.9% Glycine | 0.5 | 2.3 | 3.8 | 1.7 | 2.1 |

(% Oligomer)

The results presented in Table 2 show that for both amino acids tested, histidine and glycine, the protective effect against DAS181 dimerization was dependent on the wt % of the amine in the microparticle formulation.

EXAMPLE 6

Stabilizing Effect of Sugars Added to DAS181 Microparticle Formulations

The effect of various sugars on the stability of DAS181 microparticle formulations that include an amine was tested. Formulations were prepared essentially as described in Example 1, with various sugars being substituted for trehalose as indicated in Table 3 below (composition values corrected for residual moisture). Lyophilized samples were subjected to storage at 37° C. as bulk powder in polypropylene Eppendorf tubes (unencapsulated) or placed in two types of HPMC capsules: white/opaque or natural/clear. The samples were analyzed for the presence of DAS181 dimer at the end of one month, two months or three months using SEC.

TABLE 3

Effect of Sugars on DAS181 Dimer Formation in Microparticle Formulations Containing Glycine

| Formulation (% wt/wt) | Sugar | t = 0 | HPMC Capsules 1 mo | HPMC Capsules 2 mo | HPMC Capsules 3 mo | Unencapsulated 1 mo | Unencapsulated 2 mo | Unencapsulated 3 mo |
|---|---|---|---|---|---|---|---|---|
| 77.89% DAS181, 1.88% magnesium sulfate, 0.23% calcium chloride, 5% glycine, 15% mannitol | Mannitol | 0 | 6.01 (6.87) | 9.79 (9.95) | 12.59 (12.70)* | 3.07 | 4.12 | 5.19 |
| 77.89% DAS181, 1.88% magnesium sulfate, 0.23% calcium chloride, 5% glycine, 15% trehalose | Trehalose | 0 | 3.75 (3.83) | 5.82 (5.65) | 6.79 (7.36)* | 2.19 | 3.13 | 4.05 |

(% Oligomer)

TABLE 3-continued

Effect of Sugars on DAS181 Dimer Formation in Microparticle Formulations Containing Glycine

| Formulation | | t = | % Oligomer | | | | | |
|---|---|---|---|---|---|---|---|---|
| | | | HPMC Capsules | | | Unencapsulated | | |
| (% wt/wt) | Sugar | 0 | 1 mo | 2 mo | 3 mo | 1 mo | 2 mo | 3 mo |
| 77.89% DAS181, 1.88% magnesium sulfate, 0.23% calcium chloride, 5% glycine, 15% sucrose | Sucrose | 0 | 3.92 (3.98) | 5.67 (5.45) | 8.16 (7.94)* | 2.23 | 3.30 | 4.42 |
| 77.89% DAS181, 1.88% magnesium sulfate, 0.23% calcium chloride, 5% glycine, 15% sorbitol | Sorbitol | 0 | 4.88 (5.01) | 7.35 (7.01) | 9.52 (9.76)* | 2.16 | 3.06 | 3.89 |

*Numbers in parentheses apply to white/opaque HPMC capsules

The results in Table 3 above indicate that trehalose and sucrose protected DAS181 from oligomerization to a greater extent than did mannitol and sorbitol. In addition, mannitol-containing formulations were found to contain irregular crystals, while sucrose and trehalose form good quality microparticles.

EXAMPLE 7

Effect of Antioxidants on Oligomer Formation in DAS181 Microparticles

The effect of various antioxidants on the stability of DAS181 microparticle formulations stored at 37° C. in HPMC capsules was tested by measuring the presence of dimer at time intervals of 0, 1.5, 3 and 4.5 months. The results are shown in Table 4 below (compositions corrected for residual moisture):

TABLE 4

Effect of Antioxidants on DAS181 Stability in Microparticle Formulations

| Formulation (% | | | % Oligomer at 1.5, 3.0 or 4.5 mo | | | | | |
|---|---|---|---|---|---|---|---|---|
| | | | HPMC Capsules | | | Unencapsulated | | |
| wt/wt) | Antioxidant | t = 0 | 1.5 | 3 | 4.5 | 1.5 | 3 | 4.5 |
| 97.08% DAS181, 2.34% magnesium sulfate, 0.29% calcium chloride, 0.30% thioglycerol | Thioglycerol | 0 | 21.1 | 27 | 20.2 | 23.5 | 24.1 | 28.7 |
| 96.88% DAS181, 2.33% magnesium sulfate, 0.29% calcium chloride, 0.50% ascorbic acid | Ascorbic acid | 0 | 0.4 | 1.4 | 0.8 | 0.1 | 0.8 | 0.5 |
| 97.31% DAS181, 2.34% magnesium sulfate, 0.29% calcium chloride, 0.06% tocopherol | Tocopherol (vitamin E) | 0 | 0.6 | 3.7 | 3.2 | 0.1 | 3.1 | 5.2 |
| 97.32% DAS181, 2.34% magnesium sulfate, 0.29% calcium chloride, 0.05% melatonin | Melatonin | 0 | 2.6 | 4.5 | 5.1 | 4.6 | 4.4 | 6.0 |
| 96.88% DAS181, 2.33% magnesium sulfate, 0.29% calcium chloride, 0.50% magnesium bisulfite | Magnesium bisulfite | 0 | 1.8 | 2.8 | 2.1 | 2.7 | 3.0 | 3.0 |
| 97.37% DAS181, 2.34% magnesium sulfate, 0.29% calcium chloride | None | 0 | 3.8 | 7.2 | 6.4 | 3.0 | 5.9 | 10.1 |

Of the antioxidants tested, ascorbic acid was found to have the most protective effect against DAS181 oligomer formation. Thioglycerol was found to enhance rather than inhibit oligomer formation. The results demonstrate that antioxidants can be used to protect DAS181 microparticle formulations against oligomerization in HPMC capsules.

EXAMPLE 8

Effect of Chelators on Oligomer Formation in DAS181 Microparticles

The effect of various chelators on the stability of DAS181 microparticle formulations stored at 37° C. in HPMC capsules was tested by measuring the presence of dimer at time intervals of zero, one and three months. The results are shown in Table 5 below (compositions corrected for residual moisture):

TABLE 5

Effect of Chelators on DAS181 Stability in Microparticle Formulations

| | | % Oligomer | | | | |
|---|---|---|---|---|---|---|
| Formulation (% | Chelator-Type | | HPMC Capsules (10 mg) | | Unencapsulated | |
| wt/wt) | and wt % | t = 0 | 1 mo | 3 mo | 1 mo | 3 mo |
| 84.02% DAS181, 2.02% magnesium sulfate, 0.25% calcium chloride, 13.71% bicine | 13.7% Bicine | 0 | 5.5 | 8.7 | 2.8 | 4.7 |
| 95.84% DAS181, 2.31% magnesium sulfate, 0.29% calcium chloride, 1.56% bicine | 1.6% Bicine | 0 | 6.35 | 10.9 | 3.1 | 1.9 |
| 97.21% DAS181, 2.34% magnesium sulfate, 0.29% calcium chloride, 0.16% bicine | 0.16% Bicine | 0 | 5.3 | 9.3 | 2.7 | 5.3 |
| 70.4% DAS181, 1.69% magnesium sulfate, 0.21% calcium chloride, 27.69% DTPA | 27.7% DTPA | 0 | 8.3 | 17.6 | 2.0 | 1.9 |
| 93.78% DAS181, 2.26% magnesium sulfate, 0.28% calcium chloride, 3.69% DTPA | 3.7% DTPA | 0 | 4.75 | 8.4 | 2.4 | 4.0 |
| 97% DAS181, 2.33% magnesium sulfate, 0.29% calcium chloride, 0.38% DTPA | 0.38% DTPA | 0 | 5.0 | 8.1 | 2.2 | 4.9 |
| 85.23% DAS181, 2.05% magnesium sulfate, 0.25% calcium chloride, 12.46% TETA | 12.5% TETA | 0 | 0.8 | 1.8 | 0.7 | 1.7 |
| 96% DAS181, 2.31% magnesium sulfate, 0.29% calcium chloride, 1.4% TETA | 1.4% TETA | 0 | 1.3 | 2.9 | 0.9 | 2.7 |
| 97.23% DAS181, 2.34% magnesium sulfate, 0.29% calcium chloride, 0.14% TETA | 0.14% TETA | 0 | 2.5 | 4.4 | 1.9 | 5.3 |
| 97.37% DAS181, 2.34% magnesium sulfate, 0.29% calcium chloride | None | 0 | 5.5 | 8.7 | 2.8 | 4.7 |

Of the chelators tested, TETA was the most effective at protecting DAS181 from dimer formation in the HPMC capsules, and the greater the amount of TETA in the formulation, the less the amount of oligomer formed.

EXAMPLE 9

Combinations of Amino Acids and Sugars in DAS181 Microparticle Formulations

Combinations of several amino acids with one another and/or a sugar were tested for their ability to protect DAS181 microparticles in HPMC capsules from oligomer formation. The DAS181 microparticle formulations, prepared essentially as described in Example 1 with the ingredients set forth in Table 6 below (composition values corrected for residual moisture), were stored at 37° C. in HPMC capsules and were tested by measuring the presence of DAS181 dimer (using SEC) at time intervals of 0, 1.5, 3 and 4.5 months.

TABLE 6

Combined Effect of Amino Acids and Sugars on DAS181 Stability in Microparticle Formulations

| Formulation (% wt/wt) | Amino Acid and/or Sugar | % Oligomer at 1.5, 3.0 or 4.5 mo | | | | | | |
|---|---|---|---|---|---|---|---|---|
| | | | HPMC Capsules | | | Unencapsulated | | |
| | | t = 0 | 1.5 | 3 | 4.5 | 1.5 | 3 | 4.5 |
| 76.86% DAS181, 1.85% magnesium sulfate, 0.23% calcium chloride, 21.06% histidine | Histidine | 0 | 1.0 | 1.6 | 1.6 | 1.4 | 0.9 | 2.8 |
| 65.40% DAS181, 1.57% magnesium sulfate, 0.19% calcium chloride, 17.92% histidine, 2.55% glycine, 10.99% sucrose, 1.37% acetate | Histidine, Glycine, Sucrose, Acetate | 0 | 0.5 | 1.2 | 0.8 | 0.0 | 0.5 | 0.3 |
| 66.31% DAS181, 1.6% magnesium sulfate, 0.2% calcium chloride, 18.17% histidine, 2.59% glycine, 11.14% sucrose | Histidine, Glycine, Sucrose | 0 | 0.5 | 1.0 | 0.6 | 0.2 | 0.6 | 0.6 |
| 68.07% DAS181, 1.64% magnesium sulfate, 0.2% calcium chloride, 18.65% histidine, 11.44% sucrose | Histidine, Sucrose | 0 | 0.7 | 1.6 | 1.3 | 0.7 | 0.5 | 0.3 |
| 74.62% DAS181, 1.8% magnesium sulfate, 0.22% calcium chloride, 20.45% histidine, 2.91% glycine | Histidine (20.5%), Glycine (2.9%) | 0 | 0.8 | 2.1 | 2.0 | 0.7 | 1.3 | 0.6 |
| 74.74% DAS181, 1.8% magnesium sulfate, 0.22% calcium chloride, 20.48% histidine, 2.77% tryptophan | Histidine (20.5%), Tryptophan (2.8%) | 0 | 1.0 | 2.1 | 1.8 | 3.2 | 0.8 | 0.5 |
| 70.67% DAS181, 1.7% magnesium sulfate, 0.21% calcium chloride, 19.36% histidine, 8.06% glycine | Histidine (19.4%), Glycine (8%) | 0 | 2.6 | 4.6 | 4.5 | 3.9 | 1.0 | 2.1 |
| 52.66% DAS181, 1.27% magnesium sulfate, 0.16% calcium chloride, 36.12% histidine, 9.79% tryptophan | Histidine (36%), Tryptophan (9.8%) | 0 | 0.0 | 1.1 | 0.8 | 0.0 | 0.0 | 1.6 |
| 62.03% DAS181, 1.49% magnesium sulfate, 0.18% calcium chloride, 17% histidine, 19.29% trehalose | Histidine, Trehalose | 0 | 0.6 | 1.3 | 1.0 | 0.2 | 0.4 | 0.1 |
| 97.37% DAS181, 2.34% magnesium sulfate, 0.29% calcium chloride | None | 0 | 3.8 | 7.2 | 6.4 | 3.0 | 5.9 | 10.1 |

While histidine alone clearly had a protective effect against DAS181 oligomerization in HPMC capsules, some combinations of amino acids and sugars provided better protection in the microparticle formulations, e.g., Histidine/Glycine/Sucrose, Histidine/Trehalose and Histidine/Tryptophan especially at the higher concentration of tryptophan (9.8%).

DAS 181 (without amino terminal Met)
(SEQ ID NO: 1)

GDHPQATPAPAPDASTELPASMSQAQHLAANTATDNYRIPAITTAPNGDL

LISYDERPKDNGNGGSDAPNPNHIVQRRSTDGGKTWSAPTYIHQGTETGK

KVGYSDPSYVVDHQTGTIFNFHVKSYDQGWGGSRGGTDPENRGIIQAEVS

TSTDNGWTWTHRTITADITKDKPWTARFAASGQGIQIQHGPHAGRLVQQY

TIRTAGGAVQAVSVYSDDHGKTWQAGTPIGTGMDENKVVELSDGSLMLNS

RASDGSGFRKVAHSTDGGQTWSEPVSDKNLPDSVDNAQIIRAFPNAAPDD

PRAKVLLLSHSPNPRPWSRDRGTISMSCDDGASWTTSKVFHEPFVGYTTI

-continued

AVQSDGSIGLLSEDAHNGADYGGIWYRNFTMNWLGEQCGQKPAKRKKKGG

KNGKNRRNRKKKNP

DAS 181 (without amino terminal Met)
(SEQ ID NO: 2)

MGDHPQATPAPAPDASTELPASMSQAQHLAANTATDNYRIPAITTAPNGD

LLISYDERPKDNGNGGSDAPNPNHIVQRRSTDGGKTWSAPTYIHQGTETG

KKVGYSDPSYVVDHQTGTIFNFHVKSYDQGWGGSRGGTDPENRGIIQAEV

STSTDNGWTWTHRTITADITKDKPWTARFAASGQGIQIQHGPHAGRLVQQ

YTIRTAGGAVQAVSVYSDDHGKTWQAGTPIGTGMDENKVVELSDGSLMLN

SRASDGSGFRKVAHSTDGGQTWSEPVSDKNLPDSVDNAQIIRAFPNAAPD

DPRAKVLLLSHSPNPRPWSRDRGTISMSCDDGASWTTSKVFHEPFVGYTT

IAVQSDGSIGLLSEDAHNGADYGGIWYRNFTMNWLGEQCGQKPAKRKKKG

GKNGKNRRNRKKKNP

What is claimed is:

1. A method of making a composition comprising microparticles comprising DAS181, the method comprising:

a) providing a feedstock composition that is 8-12% (wt/wt) histidine, and further comprising DAS181, a counterion and an organic solvent; and b) cooling the composition to below 25° C., whereby a composition comprising microparticles comprising DAS181 is formed.

2. The method of claim 1, wherein the counterion is sodium sulfate.

3. The method of claim 1 wherein the counterion is magnesium sulfate.

4. The method of claim 1 wherein the feedstock composition is 70-80% (wt/wt) DAS181.

5. The method of claim 1 wherein the feedstock composition is 8-12% (wt/wt) trehalose.

6. The method of claim 1 wherein the feedstock composition is 20-30% (wt/wt) isopropanol.

7. The method of claim 1 wherein the resulting microparticles are 60% to 75% (wt/wt) a polypeptide consisting of SEQ ID NO:1 or SEQ ID NO:2, when anhydrous.

8. The method of claim 1, wherein the feedstock composition further comprises a scavenging agent.

9. A composition comprising microparticles, wherein the microparticles are about 60-70% wt/wt DAS181, 7-15% wt/wt histidine, 7-11% wt/wt trehalose, 4-8% wt/wt magnesium sulfate, and 8-12% wt/wt water.

10. The composition of claim 9 wherein the microparticles are 62%-68% (wt/wt) a polypeptide comprising SEQ ID NO:1 or a polypeptide comprising SEQ ID NO:2.

11. The composition of claim 9 wherein the microparticles have a Mass Median Aerodynamic Diameter (MMAD) of 1-8 microns, 2-8 microns or 3-8 microns.

12. The composition of claim 11 wherein the microparticles have a Geometric Standard Deviation (GSD) of 1.5-1.7, 1.3-1.6, or 1.4-1.6.

13. The composition of claim 9 wherein the weight percent of microparticles having a fine particle fractionation (FPF) below 5 microns is less than 10%.

14. A composition comprising microparticles, wherein the microparticles are about 69-74% wt/wt DAS181, 9-17% wt/wt histidine, 8-12% wt/wt trehalose, and 4-8% wt/wt magnesium sulfate.

15. The composition of claim 14 wherein the microparticles have a GSD of 1.5-1.7, 1.3-1.6, or 1.4-1.6.

16. The composition of claim 14 wherein the weight percent of microparticles having a FPF below 5 microns is less than 10%.

17. A composition comprising microparticles, wherein the microparticles are about 80-90% wt/wt DAS181, 1.5-3.5% wt/wt sodium sulfate, and 8-12% water.

18. The composition of claim 17 wherein the microparticles have a GSD of 1.2-1.8, 1.3-1.7 or 1.4-1.6.

19. The composition of claim 17 wherein the weight percent of microparticles having a fine particle fractionation (FPF) below 5 microns is less than 10%.

20. The composition of claim 9 comprising 3-6% wt/wt histidine free base and 5-9% wt/wt histidine hydrochloride.

21. The composition of claim 14 comprising 3-8% wt/wt histidine free base and 5-9% wt/wt histidine hydrochloride.

22. A composition comprising microparticles, wherein the microparticles are about 60-70% wt/wt DAS181, 8-15% wt/wt histidine, 7-11% wt/wt trehalose, 4-8% wt/wt magnesium sulfate, and 8-12% water.

23. A composition comprising microparticles, wherein the microparticles are about 69-74% wt/wt DAS181, 7-17% wt/wt histidine, 8-12% wt/wt trehalose, and 4-8% wt/wt magnesium sulfate.

* * * * *